(12) United States Patent
Chang et al.

(10) Patent No.: US 9,475,861 B2
(45) Date of Patent: Oct. 25, 2016

(54) BINDING MOLECULE HAVING INFLUENZA A VIRUS-NEUTRALIZING ACTIVITY PRODUCED FROM HUMAN B CELL

(71) Applicant: Celltrion Inc., Incheon (KR)

(72) Inventors: Shin Jae Chang, Incheon (KR); Ki Sung Kwon, Seoul (KR); Kye Sook Yi, Incheon (KR); Hyun Joo Lee, Incheon (KR); Jae Won Jeon, Incheon (KR); Hwang Keun Jun, Seoul (KR); Min Seok Chang, Incheon (KR)

(73) Assignee: Celltrion Inc., Incheon (KR)

( * ) Notice: Subject to any disclaimer, the term of this patent is extended or adjusted under 35 U.S.C. 154(b) by 0 days.

(21) Appl. No.: 14/348,284

(22) PCT Filed: Sep. 27, 2012

(86) PCT No.: PCT/KR2012/007835
§ 371 (c)(1),
(2) Date: Mar. 28, 2014

(87) PCT Pub. No.: WO2013/048153
PCT Pub. Date: Apr. 4, 2013

(65) Prior Publication Data
US 2014/0234336 A1    Aug. 21, 2014

(30) Foreign Application Priority Data

Sep. 30, 2011   (KR) .................. 10-2011-0099646

(51) Int. Cl.
*A61K 39/42*    (2006.01)
*C07K 16/10*    (2006.01)
(Continued)

(52) U.S. Cl.
CPC ..... *C07K 16/1018* (2013.01); *G01N 33/56983* (2013.01); *A61K 2039/505* (2013.01); *C07K 2317/76* (2013.01); *G01N 2333/11* (2013.01); *G01N 2500/00* (2013.01)

(58) Field of Classification Search
None
See application file for complete search history.

(56) References Cited

U.S. PATENT DOCUMENTS

| 2010/0040635 A1* | 2/2010 | Horowitz ........... C07K 16/1018 424/159.1 |
| 2011/0201547 A1* | 8/2011 | Sasisekharan ....... C07K 14/001 514/3.7 |
| 2014/0046039 A1* | 2/2014 | Ahmed .............. C07K 16/1018 530/389.4 |

FOREIGN PATENT DOCUMENTS

| CA | WO 2012009790 A1 * | 1/2012 | ........... A61K 39/145 |
| KR | 1020110102198 | 9/2011 | |

(Continued)

OTHER PUBLICATIONS

Kashyap et al., "Combinatorial antibody libraries from survivors of the Turkish H5N1 avian influenza outbreak reveal virus neutralization strategies," PNAS vol. 15, No. 16: 5986-5991 (2008).*

(Continued)

*Primary Examiner* — Janet L Andres
*Assistant Examiner* — M. Franco Salvoza
(74) *Attorney, Agent, or Firm* — McDonnell Boehnen Hulbert & Berghoff LLP

(57) ABSTRACT

The present invention relates to a binding molecule having influenza A virus-neutralizing activity derived from a human B cell, and the binding molecule having the influenza A virus-neutralizing activity, according to the present invention, is a binding molecule that is derived from a B cell that is selected from the blood of a patient infected with an influenza A virus, and has neutralizing activity against influenza A viruses, and thus is useful in preventing and treating disease derived from the influenza A virus, and can be useful in diagnosing the influenza A virus by using the binding molecule according to the present invention.

16 Claims, 6 Drawing Sheets

Figure 1:
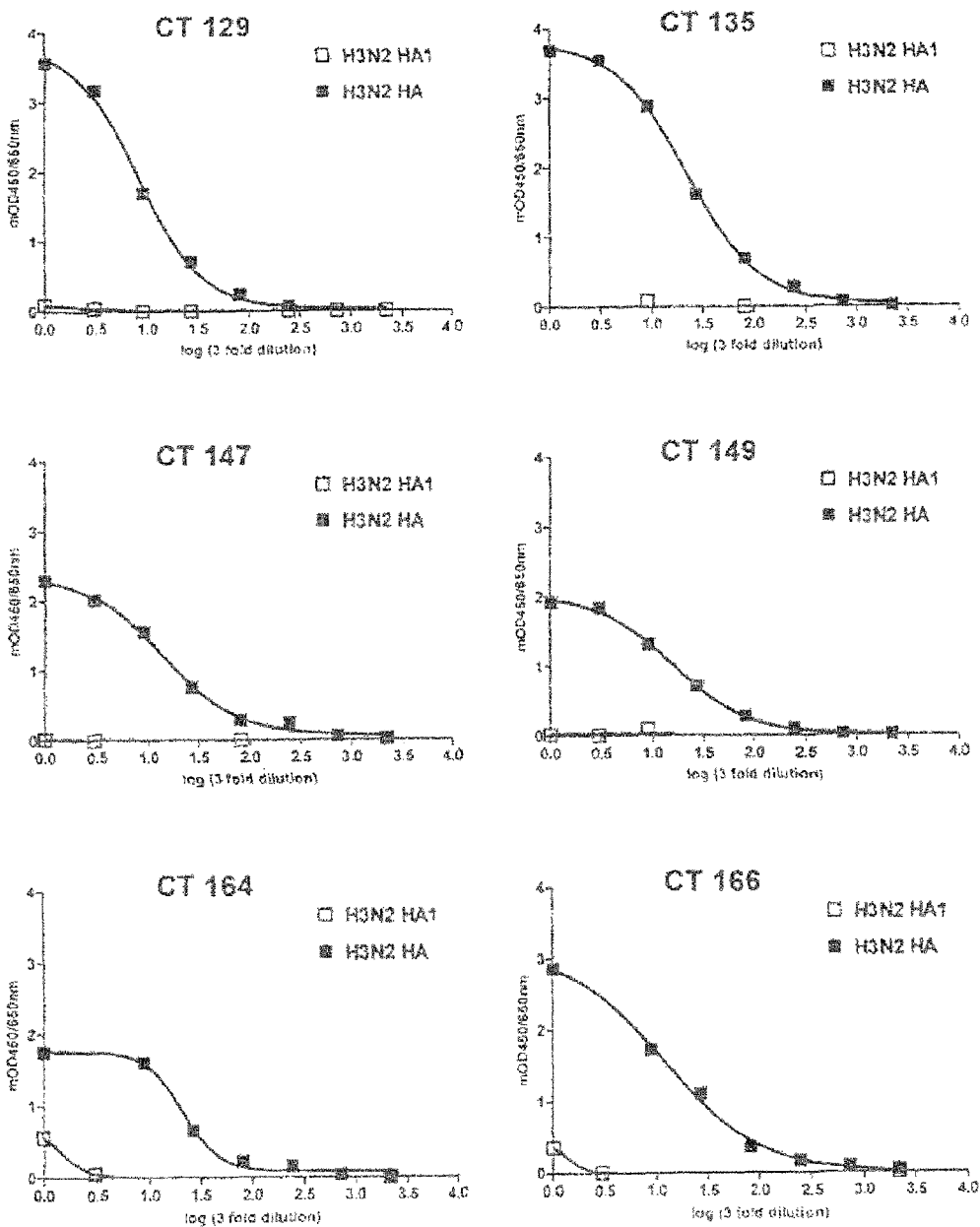

(51) Int. Cl.
*G01N 33/569* (2006.01)
*A61K 39/00* (2006.01)

(56) References Cited

FOREIGN PATENT DOCUMENTS

| WO | 2007/089753 | A2 | | 8/2007 |
|---|---|---|---|---|
| WO | 2007/134327 | | | 11/2007 |
| WO | 2007/134327 | A2 | | 11/2007 |
| WO | 2009/036157 | A1 | | 3/2009 |
| WO | 2009/121004 | A2 | | 10/2009 |
| WO | 2010/010466 | A2 | | 1/2010 |
| WO | 2010/010467 | | | 1/2010 |
| WO | 2010/132604 | A2 | | 11/2010 |
| WO | WO 2010132604 | A2 | * | 11/2010 |
| WO | 2011/111966 | A2 | | 9/2011 |

OTHER PUBLICATIONS

Huang et al., Changed epitopes drive the antigenic drift for influenza A (H3N2) viruses Bioinformatics 12(Suppl 1): S31 (2011).*

Pappas et al., "Rapid development of broadly influenza neutralizing antibodies through redundant mutations," Nature vol. 516: 418-425 (2014).*

Lingwood et al., "Structural and genetic basis for development of broadly neutralizing influenza antibodies," Nature 489: 566-570 (2012).*

Wang et al. ("Fc-Glycosylation of IgG1 is Modulated by B-cell Stimuli," Molecular & Cellular Proteomics, 10: M110.004655 (2011).*

Eibl et al., "Mammalian Cell Culture Technology: An Emerging Field," Cell and Tissue Reaction Engineering: Principles and Practice, Springer-Verlag Berlin-Heidelberg (2008).*

Scheidner et al., "Human Cell Lines for Production of Biopharmaceuticals," Cells and Culture, ESAVT Proceedings 4 (2010).*

Dumont et al., "Human cell lines for biopharmaceutical manufacturing: history, status, and future perspectives," Critical Reviews in Biotechnology, Early Online: 1-13 (2015).*

Friesen et al., "New class of monoclonal antibodies against severe influenza: prophylactic and therapeutic efficacy in ferrets", PLoS One, Feb. 8, 2010;5(2):e9106. doi: 10.1371/journal.pone.0009106.

Throsby, et al., "Heterosubtypic Neutralizing Monoclonal Antibodies Cross-Protective against H5N1 and H1N1 Recovered from Human IgM Memory B Cells", PLoS One, Dec. 16, 2008 at <http://dx.doi.org/10.1371/journal.pone.0003942>.

* cited by examiner

BINDING MOLECULE HAVING INFLUENZA A VIRUS-NEUTRALIZING ACTIVITY PRODUCED FROM HUMAN B CELL

TECHNICAL FIELD

The present invention relates to a human monoclonal antibody having neutralizing activity against influenza A virus, which is derived from human B cells selected from the blood of patients who recovered from infection with influenza A virus.

BACKGROUND ART

Influenza, an illness caused by respiratory infection with influenza viruses, often occurs in winter. It is known to have very high infectivity and to affect all age groups, particularly elderly people (Treanor J, 2004, *N Engl J. Med.* 350(3):218-20). Influenza viruses are enveloped RNA (ribonucleic acid) viruses belonging to the family Orthomyxoviridae and have a genome composed of eight negative-sense, single-stranded RNA (ribonucleic acid) segments. These influenza viruses are classified into types A, B and C. Influenza A viruses are further divided into subtypes based on their major surface proteins hemagglutinin (HA) and neuraminidase (NA). Up to date, 16 HAs and 9 NAs have been identified (Cheung T K and Poon L L 2007, *Ann N Y Acad. Sci.* 1102:1-25). Influenza viruses can affect birds, pigs and humans depending on their types and have a genome composed of RNA segments, and for this reason, their genes can continuously mutate and recombine, resulting in new genetic variations (Treanor J, 2004. *N Engl J. Med.* 350(3):218-20). Due to this continuous mutation, it is difficult to obtain permanent immunity against influenza viruses, and thus a preventive method that is currently thought to be most effective is a method of administering a vaccine against a particular type of influenza viruses expected to be prevalent each year to develop immunity against the influenza virus each year.

Vaccines against influenza viruses are generally produced using eggs, but this production method is a time-consuming and inefficient method. Accordingly, this method has a problem in that it is difficult to produce sufficient amounts of vaccines each year within a limited time frame. In an attempt to solve this problem, studies on methods of producing vaccines by cell culture have been actively conducted by several pharmaceutical companies (GSK, Baxter, etc.). In addition, if pandemic influenza virus infection occurs, it is very difficult to develop a vaccine against the infection within a short time. Also, antiviral drugs are not completely reliable due to a problem associated with the emergence of drug-resistant mutant viruses.

To overcome this problem, antibodies against influenza viruses have recently been actively developed (Throsby et al, 2008, *PloS One* 3 (e3942); Sui et al., 2009, *Nature structural & molecular biology.* 16 (265-273); Simmons et al, 2007, *PloS Medicine* 4 (e178); Wrammert et al., 2011, *J Exp Med.* 208 (181-193); Corti et al., 2011, *Science* 333 (850-856)).

Blood products from recovered patients have been used to treat patients infected with various viruses, as well as to treat pandemic flu infections. For example, when patients infected with Spanish influenza virus had symptoms of pneumonia, blood products collected from patients who recovered from infection with the influenza virus are used to treat the influenza virus (Luke et al., 2006. *Annals of internal medicine.* 145:599). As such, hyperimmune globulin (IgIv) is purified from human plasma and used to treat patients infected with various viruses, but the product obtained as described above may not be safe from potential infectious agents in blood and is inefficient for mass production.

Human B cells are used for the screening of specific human monoclonal antibodies. However, immortalization of human B cells by Epstein-Barr virus (EBV) is less efficient and time-consuming. To overcome this shortcoming, new techniques have been developed and used. One of these techniques is the use of an RT-PCR method to obtain genetic information for an antibody directly from B cells. For example, there is a method comprising staining B cells that express an antibody to a specific antigen, isolating the B cells using a FACS sorter, obtaining genetic information for the antibody from the single B cells by an RT-PCR method, inserting the genetic information into an expression vector, and transfecting the expression vector into animal cells to produce a large amount of the antibody. To perform this production method in an easier and more rapid manner, the following technique can be used. The new technique "immunospot array assay on a chip" (ISAAC) enables an antibody gene to be obtained by screening single B cells, which secrete a specific monoclonal antibody, within several weeks (Jin et al., 2009 *Nat. Med.* 15, 1088-1092). The antibody thus obtained is a natural human antibody which can be more effective in terms of immunogenic issues.

DISCLOSURE

Technical Problem

It is an object of the present invention to provide a binding molecule having neutralizing activity against influenza A virus.

Another object of the present invention is to provide an isolated nucleic acid molecule encoding the binding molecule.

Still another object of the present invention is to provide an expression vector having the isolated nucleic acid molecule inserted therein.

Still another object of the present invention is to provide a binding molecule-producing cell line transfected with the expression vector.

Still another object of the present invention is to provide a method for screening a binding molecule.

Still another object of the present invention is to provide a composition comprising the binding molecule.

Still another object of the present invention is to provide a method of treating a disease caused by influenza A virus using the binding molecule.

Still another object of the present invention is to provide a method of preventing a disease caused by influenza A virus using the binding molecule.

Still another object of the present invention is to provide a method for diagnosing influenza A virus infection using the binding molecule.

Still another object of the present invention is to provide a kit for diagnosis of influenza A virus, which comprises the binding molecule.

Technical Solution

In order to achieve the above objects, the present invention provides a binding molecule having neutralizing activity against influenza A virus.

The present invention also provides an isolated nucleic acid molecule encoding the binding molecule.

The present invention also provides an expression vector having the isolated nucleic acid molecule inserted therein.

The present invention also provides a binding molecule-producing cell line transfected with the expression vector.

The present invention also provides a method for screening a binding molecule.

The present invention also provides a composition comprising the binding molecule.

The present invention also provides a composition for preventing and treating a disease caused by an influenza A virus, which comprises the binding molecule.

The present invention also provides a composition for diagnosis of influenza A virus, which comprises the binding molecule.

The present invention also provides a method of treating a disease caused by influenza A virus using the binding molecule.

The present invention also provides a method of preventing a disease caused by influenza A virus using the binding molecule.

The present invention also provides a method of diagnosing influenza A virus infection using the binding molecule.

The present invention also provides a kit for diagnosis of influenza A virus, which comprises the binding molecule.

Advantageous Effects

The binding molecule of the present invention has binding affinity for and neutralizing activity against influenza A virus, and thus is useful for the prevention and treatment of a disease caused by the influenza A virus and is also useful for diagnosis of influenza A virus infection.

DESCRIPTION OF DRAWINGS

FIG. 1 is a set of graphs showing the results of ELISA performed to verify the binding affinities of primarily screened binding molecules to H3 hemagglutinin (hereinafter referred to as "HA").

FIG. 2 shows maps of vectors pCT145 (A) and pCT147 (B).

A: pCT145 vector;

B: pCT147 vector;

pac: a gene which encodes a Puromycin N-acetyl-tranferase (PAC); and

DS: dyad symmetry sequence (EBNA1 binds to the dyad symmetry (DS) element in oriP).

FIG. 3 is a map of an expression vector expressing the binding molecule of the present invention.

FIG. 4 shows the results of animal (mouse) experiments conducted using the binding molecule of the present invention.

FIG. 5 shows the results of measuring the virus titer-change in nasal wash and lung tissue after infection with H3N2 (A/Hongkong/68) influenza virus during animal (ferret) experiments conducted using the binding molecule of the present invention.

FIG. 6 shows the results of measuring the virus titer-change in nasal wash and lung tissue after infection with H5N1 (A/Vietnam/1203/04) influenza virus during animal (ferret) experiments conducted using the binding molecule of the present invention.

BEST MODE

Hereinafter, terms used herein will be defined as follows.

The term "influenza A viruses" as used herein refers to enveloped viruses belonging to the family Orthomyxoviridae and having a genome composed of eight negative-sense, single-stranded RNA (ribonucleic acid) segments. These influenza viruses are classified into types A, B and C, and the influenza A viruses are further divided into subtypes based on their major surface proteins HA (hemagglutinin) and NA (neuraminidase). 16 HAs and 9 NAs have been reported to date.

As used herein, the expression "H3 subtype viruses" refers to viruses having the H3-subtype HA, and thus is intended to comprise H3N1, H3N2, H3N3, H3N4, H3N5, H3N6, H3N7, H3N8 and H3N9 viruses.

As used herein, the term "hemagglutinin" (hereinafter referred to as "HA") indicates the envelope glycoprotein of influenza virus. HA mediates the adsorption and penetration of influenza virus into a host cell. 16 HA subtypes have been reported to date.

The term "recovered or completely recovered patients" as used herein refers to patients who were positive for influenza A virus due to influenza A virus infection, but are negative for influenza A virus in the blood after a given period of time.

As used herein, the term "binding molecule" refers to an intact immunoglobulin comprising monoclonal antibodies, such as chimeric, humanized or human monoclonal antibodies, or to an antigen-binding or variable-domain-comprising fragment of an immunoglobulin that competes with the intact immunoglobulin for specific binding to the binding partner of the immunoglobulin, for example, the monomeric HA or trimeric HA of influenza A virus. Regardless of structure, the antigen-binding fragment binds with the same antigen that is recognized by the intact immunoglobulin. An antigen-binding fragment can comprise a peptide or polypeptide comprising an amino acid sequence consisting of at least 2, 20, 25, 30, 35, 40, 50, 60, 70, 80, 90, 100, 125, 150, 175, 200, or 250 contiguous amino acid residues of the amino acid sequence of the binding molecule. Antigen-binding fragments comprise, inter alia, Fab, F(ab'), $F(ab')_2$, Fv, dAb, Fd, complementarity determining region (CDR) fragments, single-chain antibodies (scFv), bivalent single-chain antibodies, single-chain phage antibodies, diabodies, triabodies, tetrabodies, polypeptides that contain at least one fragment of an immunoglobulin that is sufficient to confer specific antigen binding to the polypeptide, etc. The above fragments may be produced synthetically or by enzymatic or chemical cleavage of intact immunoglobulins or they may be genetically engineered by recombinant DNA techniques. The methods of production are well known in the art.

As used herein, the term "pharmaceutically acceptable excipient" means any inert substance that is combined with an active molecule such as a drug, agent, or binding molecule for preparing an agreeable or convenient dosage form. The pharmaceutically acceptable excipient is an excipient that is non-toxic to recipients at the used dosages and concentrations, and is compatible with other ingredients of the formulation comprising the drug, agent or binding molecule.

As used herein, the term "therapeutically effective amount" refers to an amount of the binding molecule that is effective for preventing or treating a condition resulting from infection with influenza A virus.

Hereinafter, the present invention will be described in detail.

The present inventors isolated peripheral blood mononuclear cells (PBMCs) from blood collected from patients who recovered from infection with influenza A virus. B cells that produce monoclonal antibodies against the H1-subtype HA were screened from the isolated PBMCs using the ISAAC method. The genetic information for producing monoclonal antibodies against HA in the screened B cells was obtained by an RT-PCR method and inserted into PCDNA™ vectors. The vectors were transfected into a CHO cell line, and then 82 antibodies were primarily selected. To more accurately measure binding affinity to HA, all the antibodies inserted into the PCDNA™ vector were transfected into human F2N cells, and antibodies generated from the transfected cells were comparatively analyzed by HA-ELISA using the monomeric HA and trimeric HA of H3 subtype as antigens, thereby secondarily selecting 6 antibodies (CT129, CT135, CT147, CT149, CT163 and CT166 antibodies) that reacted with the trimeric HA at a higher degree than with the monomeric HA. In order examine the neutralizing activities of the selected antibodies against various influenza viruses, a microneutralization test (hereinafter referred to as "MN test") and a hemagglutination inhibition test (hereinafter referred to as "HI test") were performed. A number of the antibodies exhibited high or low neutralizing activities against various influenza viruses, but all the antibodies showed a negative reaction in the HI test. Through the MN test, the CT149 antibody showing neutralizing activity against various viruses was selected. The gene of the selected antibody was inserted into the MarEx expression vector having high antibody expression efficiency, and then the vector was transfected into F2N cells. The antibody derived from the transfected cells was subjected to the MN test for more various influenza viruses. As a result, it was shown that the CT149 antibody had neutralizing activity not only H1 and H3 subtype viruses, but also H5, H7 and H9 subtype viruses (see Table 4). In addition, in animal experiments conducted using H3-subtype influenza virus, the CT149 antibody exhibited excellent preventive and therapeutic effects against H3N2 infection (see FIG. 4). Based on the above-described results; the present inventors have completed an invention relating to an anti-influenza A virus monoclonal antibody that protects against influenza A virus infection.

Accordingly, the present invention provides a binding molecule having neutralizing activity against influenza A virus.

The binding molecule is preferably an antibody. The antibody is preferably a Fab fragment, a Fv fragment, a diabody, a chimeric antibody, a humanized antibody or a human antibody, but is not limited thereto.

In the present invention, the binding molecule binds to HA on the surface of influenza A virus. Also, the binding molecule is preferably derived from B cells present in the blood of patients who recovered from infection with the influenza A virus H1N1 subtype.

Particularly, the CT149 antibody has neutralizing activity not only against group 1 (H1, H5 and H9) influenza viruses, but also against group 2 (H3 and H7) influenza viruses.

In the present invention, the influenza A virus may be of the H1N1 subtype, and the influenza A virus H1N1 subtype may be A/Ohio/07/2009. Also, the influenza A virus may be of the H5N1 subtype, and the influenza A virus H5N1 subtype may be A/Vietnam/1203/04×PR8. In addition, the influenza A virus may be of the H7N2 subtype, and the influenza A virus H7N2 subtype may be A/turkey/Virginia/02×PR8. Moreover, the influenza A virus may be of the H9N2 subtype, and the influenza A virus H9N2 subtype may be any one or more selected from the group consisting of A/Green-winged teal/209/TX/2009 and A/ck/HK/G9/97×PR8. Also, in the present invention, the influenza A virus may be of the H3N2 subtype, and the influenza A virus H3N2 subtype may be any one or more selected from the group consisting of A/Brisbane/10/07, A/Wisconsin/67/05, A/Wyomin/3/03.rg, A/Beijing/353/89-X109, A/Beijing/32/92-R-H3, A/Johannesburg/33/94 R-H3, A/Nanchang/933/95, A/Sydney/5/97, and A/Panama/2007/99.

In the present invention, the complementarity determining regions (CRDs) of variable domains were determined using a conventional method according to the system designed by Kabat et al. (see Kabat et al., Sequences of Proteins of Immunological Interest ($5^{th}$), National Institutes of Health, Bethesda, Md. (1991)). CDR numbering used in the present invention was performed according to the Kabat method, but the present invention also encompasses binding molecules comprising CDRs determined by other methods, comprising the IMGT method, the Chothia method, and the AbM method.

The present invention also provides a binding molecule having neutralizing activity against influenza A virus, which comprises the following light-chain polypeptide sequence: a light chain comprising, as determined according to the Kabat method, any one of CDR1 region selected from the group consisting of polypeptide sequences set forth in SEQ ID NOS: 1, 7, 13 and 15, any one of CDR2 region selected from the group consisting of polypeptide sequences set forth in SEQ ID NOS: 2, 8 and 16, and any one of CDR3 region selected from the group consisting of polypeptide sequences set forth in SEQ ID NOS: 3 or 9.

The present invention also provides a binding molecule having neutralizing activity against influenza A virus, which comprises the following heavy-chain polypeptide sequence: a heavy chain comprising, as determined according to the Kabat method, any one of CDR1 region selected from the group consisting of polypeptide sequences set forth in SEQ ID NOS: 4 or 10, any one of CDR2 region selected from the group consisting of polypeptide sequences set forth in SEQ ID NOS: 5, 11, 14 and 17, and any one of CDR3 region selected from the group consisting of polypeptide sequences set forth in SEQ ID NOS: 6 or 12.

The present invention also provides a binding molecule having neutralizing activity against influenza A virus, which comprises the following light-chain and heavy-chain polypeptide sequences: a light chain comprising, as determined according to the Kabat method, any one of CDR1 region selected from the group consisting of polypeptide sequences set forth in SEQ ID NOS: 1, 7, 13 and 15, any one of CDR2 region selected from the group consisting of polypeptide sequences set forth in SEQ ID NOS: 2, 8 and 16, and any one of CDR3 region selected from the group consisting of polypeptide sequences set forth in SEQ ID NOS: 3 or 9; and a heavy chain comprising, as determined according to the Kabat method, any one of CDR1 region selected from the group consisting of polypeptide sequences set forth in SEQ ID NOS: 4 or 10; any one of CDR2 region selected from the group consisting of polypeptide sequences set forth in SEQ ID NOS: 5, 11, 14 and 17; and any one of CDR3 region selected from the group consisting of polypeptide sequences set forth in SEQ ID NOS: 6 or 12.

The present invention also provides a binding molecule having neutralizing activity against influenza A virus, which comprises any one polypeptide sequence selected from the group consisting of the following polypeptide sequences: a binding molecule composed of a light chain comprising, as determined according to the Kabat method, a CDR1 region set forth in SEQ ID NO: 1, a CDR2 region set forth in SEQ ID NO: 2, and a CDR3 region set forth in SEQ ID NO: 3, and a heavy chain comprising, as determined according to the Kabat method, a CDR1 region set forth in SEQ ID NO: 4, a CDR2 region set forth in SEQ ID NO: 5, and a CDR3 region set forth in SEQ ID NO: 6; a binding molecule composed of a light chain comprising, as determined according to the Kabat method, a CDR1 region set forth in SEQ ID NO: 7, a CDR2 region set forth in SEQ ID NO: 8, and a CDR3 region set forth in SEQ ID NO: 9, and a heavy chain comprising, as determined according to the Kabat method, a CDR1 region set forth in SEQ ID NO: 10, a CDR2 region set forth in SEQ ID NO: 11, and a CDR3 region set forth in SEQ ID NO: 12; a binding molecule composed of a light chain comprising, as determined according to the Kabat method, a CDR1 region set forth in SEQ ID NO: 13, a CDR2 region set forth in SEQ ID NO: 8, and a CDR3 region set forth in SEQ ID NO: 9, and a heavy chain comprising, as determined according to the Kabat method, a CDR1 region set forth in SEQ ID NO: 10, a CDR2 region set forth in SEQ ID NO: 14, and a CDR3 region set forth in SEQ ID NO: 6; and a binding molecule composed of a light chain comprising, as determined according to the Kabat method, a CDR1 region set forth in SEQ ID NO: 15, a CDR2 region set forth in SEQ ID NO: 16, and a CDR3 region set forth in SEQ ID NO: 9, and a heavy chain comprising, as determined according to the Kabat method, a CDR1 region set forth in SEQ ID NO: 10, a CDR2 region set forth in SEQ ID NO: 17, and a CDR3 region set forth in SEQ ID NO: 12.

In the present invention, the binding molecule is preferably composed of a light chain comprising a polypeptide sequence set forth in SEQ ID NO: 37, and a heavy chain comprising a polypeptide sequence set forth in SEQ ID NO: 38.

In the present invention, the binding molecule is preferably composed of a light chain comprising a polypeptide sequence set forth in SEQ ID NO: 39, and a heavy chain comprising a polypeptide sequence set forth in SEQ ID NO: 40.

In the present invention, the binding molecule is preferably composed of a light chain comprising a polypeptide sequence set forth in SEQ ID NO: 41, and a heavy chain comprising a polypeptide sequence set forth in SEQ ID NO: 42.

In addition, the binding molecule is preferably composed of a light chain comprising a polypeptide sequence set forth in SEQ ID NO: 43, and a heavy chain comprising a polypeptide sequence set forth in SEQ ID NO: 44.

The binding molecule preferably has neutralizing activity against any one selected from the group consisting of influenza A virus H1, H3, H5, H7 and H9 subtypes. Also, the influenza A virus H3 subtype is preferably H3N2, but is not limited thereto.

The present invention also provides a binding molecule having neutralizing activity against influenza A virus, which comprises the following light-chain polynucleotide sequence: a light chain comprising, as determined according to the Kabat method, any one of CDR1 region selected from the group consisting of polynucleotide sequences set forth in SEQ ID NOS: 18, 24, and 34, any one of CDR2 region selected from the group consisting of polynucleotide sequences set forth in SEQ ID NOS: 19, 25 and 35, and any one of CDR3 region selected from the group consisting of polynucleotide sequences set forth in SEQ ID NOS: 20 or 26.

The present invention also provides a binding molecule having neutralizing activity against influenza A virus, which comprises the following heavy-chain polynucleotide sequence: a heavy chain comprising, as determined according to the Kabat method, any one of CDR1 region selected from the group consisting of polynucleotide sequences set forth in SEQ ID NOS: 21, 27 and 31, any one of CDR2 region selected from the group consisting of polynucleotide sequences set forth in SEQ ID NOS: 22, 28, 32 and 36, and any one of CDR3 region selected from the group consisting of polynucleotide sequences set forth in SEQ ID NOS: 23, 29 and 33.

The present invention also provides a binding molecule having neutralizing activity against influenza A virus, which comprises the following light-chain and heavy-chain polynucleotide sequences: a light chain comprising, as determined according to the Kabat method, any one of CDR1 region selected from the group consisting of polynucleotide sequences set forth in SEQ ID NOS: 18, 24, 30 and 34, any one of CDR2 region selected from the group consisting of polynucleotide sequences set forth in SEQ ID NOS: 19, 25 and 35, and any one of CDR3 region selected from the group consisting of polynucleotide sequences set forth in SEQ ID NOS: 20 or 26; and a heavy chain comprising, as determined according to the Kabat method, any one of CDR1 region selected from the group consisting of polynucleotide sequences set forth in SEQ ID NOS: 21, 27 and 31, any one of CDR2 region selected from the group consisting of polynucleotide sequences set forth in SEQ ID NOS: 22, 28, 32 and 36, and any one of CDR3 region selected from the group consisting of polynucleotide sequences set forth in SEQ ID NOS: 23, 29 and 33.

The present invention also provides a binding molecule having neutralizing activity against influenza A virus, which is composed of a polynucleotide sequence selected from the group consisting of the following polynucleotide sequences: a binding molecule composed of a light chain comprising, as determined according to the Kabat method, a CDR1 region set forth in SEQ ID NO: 18, a CDR2 region set forth in SEQ ID NO: 19, and a CDR3 region set forth in SEQ ID NO: 20, and a heavy chain comprising, as determined according to the Kabat method, a CDR1 region set forth in SEQ ID NO: 21, a CDR2 region set forth in SEQ ID NO: 22, and a CDR3 region set forth in SEQ ID NO: 23; a binding molecule composed of a light chain comprising, as determined according to the Kabat method, a CDR1 region set forth in SEQ ID NO: 24, a CDR2 region set forth in SEQ ID NO: 25, and a CDR3 region set forth in SEQ ID NO: 26, and a heavy chain comprising, as determined according to the Kabat method, a CDR1 region set forth in SEQ ID NO: 27, a CDR2 region set forth in SEQ ID NO: 28, and a CDR3 region set forth in SEQ ID NO: 29; a binding molecule composed of a light chain comprising, as determined according to the Kabat method, a CDR1 region set forth in SEQ ID NO: 30, a CDR2 region set forth in SEQ ID NO: 25, and a CDR3 region set forth in SEQ ID NO: 26, and a heavy chain comprising, as determined according to the Kabat method, a CDR1 region set forth in SEQ ID NO: 31, a CDR2 region set forth in SEQ ID NO: 32, and a CDR3 region set forth in SEQ ID NO: 33; and a binding molecule composed of a light chain comprising, as determined according to the Kabat method, a CDR1 region set forth in SEQ ID NO: 34, a CDR2 region set forth in SEQ ID NO: 35, and a CDR3 region set forth in SEQ ID NO: 26, and a heavy chain comprising, as determined according to the Kabat method, a CDR1 region set forth in SEQ ID NO: 31, a CDR2 region set forth in SEQ ID NO: 36, and a CDR3 region set forth in SEQ ID NO: 29.

In the present invention, the binding molecule is preferably composed of a light chain comprising a polynucleotide sequence set forth in SEQ ID NO: 45, and a heavy chain comprising a polynucleotide sequence set forth in SEQ ID NO: 46.

Also, the binding molecule is preferably composed of a light chain comprising a polynucleotide sequence set forth in SEQ ID NO: 47, and a heavy chain comprising a polynucleotide sequence set forth in SEQ ID NO: 48.

Moreover, the binding molecule is preferably composed of a light chain comprising a polynucleotide sequence set forth in SEQ ID NO: 49, and a heavy chain comprising a polynucleotide sequence set forth in SEQ ID NO: 50.

In addition, the binding molecule is preferably composed of a light chain comprising a polynucleotide sequence set forth in SEQ ID NO: 51, and a heavy chain comprising a polynucleotide sequence set forth in SEQ ID NO: 52.

The binding molecule preferably has neutralizing activity against any one selected from the group consisting of influenza A virus H1, H3, H5, H7 and H9 subtypes. Also, the influenza A virus H3 subtype is preferably H3N2, but is not limited thereto.

The binding molecule of the present invention is preferably an antibody, but is not limited thereto. The antibody is preferably a Fab fragment, a Fv fragment, a diabody, a chimeric antibody, a humanized antibody or a human antibody. Further, the present invention encompasses all antibody fragments that have the ability to bind to the influenza A virus HA and that bind to the HA competitively with the binding molecule of the present invention. In addition, the present invention also encompasses functional variants of the binding molecule. If variants of the binding molecule can complete with the binding molecule of the present invention for binding specifically to the influenza A virus H3 subtype, or fragments thereof, they are regarded as functional variants of the binding molecule of the present invention. Specifically, if functional variants can bind to the influenza A virus HA, or fragments thereof, and have neutralizing activity against such an HA or fragments, they are regarded as the functional variants of the present invention. Functional variants comprise, but are not limited to, derivatives that are substantially similar in primary structural sequence, which but contain, for example, in vitro or in vivo modifications, chemical and/or biochemical, that are not found in the parent binding molecule of the present invention. Such modifications comprise, for example, acetylation, acylation, covalent attachment of a nucleotide or nucleotide derivative, covalent attachment of a lipid or lipid derivative, cross-linking, disulfide bond formation, glycosylation, hydroxylation, methylation, oxidation, pegylation, proteolytic processing, phosphorylation, and the like. Alternatively, functional variants can be binding molecules comprising an amino acid sequence containing substitutions, insertions, deletions or combinations thereof of one or more amino acids compared to the amino acid sequences of the parental binding molecules. Furthermore, functional variants can comprise truncations of the amino acid sequence at either or both of the amino or carboxyl termini. Functional variants according to the present invention may have the same or different, either higher or lower, binding affinities compared to the parental monoclonal antibody but are still capable of binding to the influenza A virus HA, or fragments thereof. For example, functional variants according to the invention may have increased or decreased binding affinities for the influenza A virus HA, or fragments thereof, compared to the parental binding molecules of the present invention. Preferably, the amino acid sequences of the variable regions, comprising, but not limited to, framework regions, hypervariable regions, in particular the CDR3 regions, are modified. Generally, the light-chain or heavy-chain regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope of the present invention have at least about 50-99%, preferably at least about 60-99%, more preferably at least about 80-99%, even more preferably at least about 90-99%, in particular at least about 95-99%, and in particular at least about 97-99% amino acid sequence homology with the parental monoclonal antibody as defined herein. Computer algorithms such as Gap or Best fit known to a person skilled in the art can be used to optimally align amino acid sequences to be compared and to define similar or identical amino acid residues. Functional variants can be obtained either by altering the parental monoclonal antibodies or parts thereof by general molecular biology methods known in the art comprising PCR, oligonucleotide-directed mutagenesis and site-directed mutagenesis, or by organic synthetic methods, but are not limited thereto.

The present invention also provides an isolated nucleic acid molecule encoding the binding molecule of the present invention.

The nucleic acid molecule of the present invention encompasses all nucleic acid molecules obtained by translating the amino acid sequences of the antibodies of the present invention to polynucleotide sequences according to methods known to those skilled in the art. Accordingly, various polynucleotide sequences with open reading frames (ORFs) can be prepared and are also comprised in the scope of the nucleic acid molecules of the present invention.

The present invention also provides an expression vector having the isolated nucleic acid molecule inserted therein. The expression vector can preferably be derived from any one selected from the group consisting of, but not limited to, an MarEx expression vector produced by Celltrion Inc. (Korea), a commercially widely available PCDNA™: vector, F, R1, RP1 Col, pBR322, ToL, Ti vector; cosmids; phages such as lambda, larribdoid, M13, Mu, P1, P22, Qμ, T-even, T2, T4, T7, etc; and plant viruses. Any expression vector known to those skilled in the art may be used in the present invention, and the choice of the expression vector is dependent on the nature of the host cell of choice. Introduction of the vector in host cells can be effected by, but not limited to, calcium phosphate transfection, virus infection, DEAE-dextran mediated transfection, lipofectamin transfection or electroporation, and any person skilled in the art can select and use an introduction method suitable for the expression vector and host cell used. Preferably, the vector contains one or more selectable markers, but is not limited thereto, and a vector containing no selectable marker may also be used. The choice of the selectable markers may depend on the host cells of choice, although this is not critical to the present invention as is well known to those skilled in the art.

To facilitate the purification of the nucleic acid molecule of the present invention, a tag sequence may be inserted into the expression vector. Examples of the tag comprise, but are not limited to, a hexa-histidine tag, a hemagglutinin tag, a myc tag or a FLAG tag. Any tag facilitating purification, known to those skilled in the art, may be used in the present invention.

The present invention also provides a cell line that produces a binding molecule having neutralizing activity against influenza A virus, the cell line having the above-described expression vector transfected therein.

In the present invention, the cell line may comprise cells of mammalian, plant, insect cell, fungal or bacterial origin, but is not limited thereto. As the mammalian cell, any one selected from the group consisting of but not limited to, CHO cells, F2N cells, CSO cells, BHK cells, Bowes melanoma cells, HeLa cells, 911 cells, AT1080 cells, A549 cells, HEK 293 cells and HEK293T cells, is preferably used as a host cell. Any cell usable as a mammalian host cell, known to those skilled in the art, may be used in the present invention.

The present invention also provides a method of screening a binding molecule, which has neutralizing activity against influenza A virus, from patients infected with influenza A virus, the method comprising the steps of: 1) screening a patient, whose blood is negative for influenza A virus, from patients infected with influenza A virus; 2) collecting blood from the patient screened in step 1); 3) isolating B cells from the patient's blood collected in step 2); 4) screening B cells, which produce a binding molecule that binds to hemagglutinin (HA), from the B cells isolated in step 3); 5) extracting RNAs from the B cells screened in step 4); 6) amplifying binding molecule genes from the RNAs extracted in step 5); 7) cloning the genes, amplified in step 6), into expression vectors; 8) transfecting the expression vectors of step 7) into host cells; 9) screening binding molecules, which bind to HA, from binding molecules derived from the transfected cells constructed in step 8); 10) preparing and culturing a cell line for the screened binding molecules; 11) purifying binding molecules, which bind to the HA of influenza A virus, from the cell culture of step 10); 12) reconfirming whether the binding molecules purified in step 11) have neutralizing activity against influenza A virus; and 13) screening a binding molecule confirmed to have neutralizing activity against influenza A virus in step 12).

The binding molecule in the above-described screening method is preferably an antibody, but is not limited thereto. The antibody is preferably a Fab fragment, a Fv fragment, a diabody, a chimeric antibody, a humanized antibody or a human antibody. Further, the present invention encompasses all antibody fragments that have the ability to bind to the influenza A virus HA and that bind to the HA competitively with the binding molecule of the present invention.

In addition, the present invention also encompasses functional variants of the binding molecule. If variants of the binding molecule can complete with the binding molecule of the present invention for binding specifically to the influenza A virus H3 subtype, or fragments thereof, they are regarded as functional variants of the binding molecule of the present invention. Specifically, if functional variants can bind to the influenza A virus HA, or fragments thereof, and have neutralizing activity against such an HA or fragments, they are regarded as the functional variants of the present invention. Functional variants comprise, but are not limited to, derivatives that are substantially similar in primary structural sequence, which but contain, for example, in vitro or in vivo modifications, chemical and/or biochemical, that are not found in the parent binding molecule of the present invention. Such modifications comprise, for example, acetylation, acylation, covalent attachment of a nucleotide or nucleotide derivative, covalent attachment of a lipid or lipid derivative, cross-linking, disulfide bond formation, glycosylation, hydroxylation, methylation, oxidation, pegylation, proteolytic processing, phosphorylation, and the like. Alternatively, functional variants can be binding molecules comprising an amino acid sequence containing substitutions, insertions, deletions or combinations thereof of one or more amino acids compared to the amino acid sequences of the parental monoclonal antibodies. Furthermore, functional variants can comprise truncations of the amino acid sequence at either or both of the amino or carboxyl termini. Functional variants according to the present invention may have the same or different, either higher or lower, binding affinities compared to the parental monoclonal antibody but are still capable of binding to the influenza A virus HA, or fragments thereof. For example, functional variants according to the invention may have increased or decreased binding affinities for the influenza A virus HA, or fragments thereof, compared to the parental binding molecules. Preferably, the amino acid sequences of the variable regions, comprising, but not limited to, framework regions, hypervariable regions, in particular the CDR3 regions, are modified. Generally, the light-chain or heavy-chain regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope of the present invention have at least about 50-99%, preferably at least about 60-99%, more preferably at least about 80-99%, even more preferably at least about 90-99%, in particular at least about 95-99%, and in particular at least about 97-99% amino acid sequence homology with the parental monoclonal antibody as defined herein. Computer algorithms such as Gap or Best fit known to a person skilled in the art can be used to optimally align amino acid sequences to be compared and to define similar or identical amino acid residues. Functional variants can be obtained either by altering the parental monoclonal antibodies or parts thereof by general molecular biology methods known in the art comprising PCR, oligonucleotide-directed mutagenesis and site-directed mutagenesis, or by organic synthetic methods, but are not limited thereto.

The present invention also provides a composition comprising the above-described binding molecule.

The composition of the present invention may comprise, in addition to the binding molecule having neutralizing activity against influenza A virus, a pharmaceutically acceptable excipient. Pharmaceutically acceptable excipients are well known to those skilled in the art.

The present invention also provides a composition for preventing and treating a disease caused by influenza A virus, the composition comprising the above-described binding molecule.

The preventive and therapeutic composition of the present invention may comprise, in addition to the binding molecule having neutralizing activity against influenza A virus, a pharmaceutically acceptable excipient. Pharmaceutically acceptable excipients are well known to those skilled in the art.

Further, the preventive and therapeutic composition of the present invention may comprise at least five other therapeutic agents. The preventive and therapeutic composition of the present invention may comprise various monoclonal antibodies that bind to the influenza A virus HA, or fragments thereof, and thus can exhibit a synergistic effect on neutralizing activity.

In addition, the preventive and therapeutic composition of the present invention may further comprise one or more other therapeutic agents or diagnostic agents. The therapeutic agents comprise, but are not limited to, anti-viral drugs. Examples of such drugs comprise antibodies, small molecules, organic or inorganic compounds, enzymes, polynucleotide sequences, anti-viral peptides, etc.

The preventive and therapeutic composition of the present invention must be sterile and stable under the conditions of manufacture and storage. Also, it can be in the form of powder to be reconstituted in an appropriate pharmaceutically acceptable excipient before or at the time of delivery. In the case of sterile powders for the preparation of sterile injectable solutions, preferred preparation methods are vacuum drying and freeze-drying that yield a powder of the active ingredient and any additional desired ingredient from a previously sterile-filtered solution of the powder. Alternatively, the composition of the present invention can be in solution and an appropriate pharmaceutically acceptable excipient can be added and/or mixed before or at the time of delivery to provide a unit dosage injectable form. Preferably, the pharmaceutically acceptable excipient that is used in the present invention is suitable for high drug concentration, can maintain proper flowability and, if necessary, can delay absorption.

The choice of the optimal route of administration of the preventive and therapeutic composition of the present invention will be influenced by several factors comprising the physico-chemical properties of the active molecules within the composition, the urgency of the clinical situation and the relationship of the plasma concentrations of the active molecules to the desired therapeutic effect. For example, the binding molecule of the present invention can be prepared with carriers that will protect them against rapid release, such as controlled release formulations, comprising implants and microencapsulated delivery systems. Biodegradable and biocompatible polymers, such as ethylene vinyl acetate, polyanhydrides, polyglycolic acid, collagen, polyorthoesters, and polylactic acid, may be used in the present invention. Furthermore, the binding molecule of the present invention may be coated or co-administered with a material or compound that prevents the inactivation of the antibody. For example, the binding molecule of the present invention may be administered together with an appropriate carrier, for example, liposome or a diluent.

The routes of administration of the preventive and therapeutic composition of the present invention can be divided into oral and parenteral routes. The preferred administration route is an intravenous, subcutaneous or intranasal route, but is not limited thereto.

Oral dosage forms can be formulated as tablets, troches, lozenges, aqueous or oily suspensions, dispersible powders or granules, emulsions, hard capsules, soft gelatin capsules, syrups or elixirs, pills, dragees, liquids, gels, or slurries. These formulations can contain pharmaceutical excipients comprising, but not limited to, inert diluents, granulating and disintegrating agents, binding agents, lubricating agents, preservatives, coloring agents, flavoring or sweetening agents, vegetable or mineral oils, wetting agents, and thickening agents.

Formulations for parenteral administration can be in the form of aqueous or non-aqueous isotonic sterile non-toxic injection or infusion solutions or suspensions. The solutions or suspensions may comprise agents that are non-toxic to recipients at the dosages and concentrations employed such as 1,3-butanediol, Ringer's solution, Hank's solution, isotonic sodium chloride solution, oils, fatty acids, local anaesthetic agents, preservatives, buffers, viscosity or solubility-increasing agents, water-soluble antioxidants, oil-soluble antioxidants and metal chelating agents.

The present invention also provides a composition for diagnosis of influenza A virus, which comprises a conjugate comprising a tag linked to the above-described binding molecule having neutralizing activity against anti-influenza A virus.

The composition for diagnosis according to the present invention comprises at least one detectable tag, such as a detectable moiety/agent. The tag can be linked non-covalently to the binding molecule of the present invention. The tag can also be linked directly to the binding molecule through covalent bonding. Alternatively, the tag can also be linked to the binding molecule by means of one or more linking compounds. Techniques for linking the tag to the binding molecule are well known to those skilled in the art. The detectable moiety/agent as the tag is preferably any one selected from the group consisting of enzymes, prosthetic groups, fluorescent materials, luminescent materials, bioluminescent materials, radioactive materials, positron emitting metals, and non-radioactive paramagnetic metal ions, but is not limited thereto.

The present invention also provides a method for treatment of a disease caused by influenza A virus, the method comprising administering to a subject having the disease a therapeutically effective amount of the inventive binding molecule having neutralizing activity against influenza A virus.

In the therapeutic method of the present invention, the influenza A virus is preferably any one selected from the group consisting of H1, H3, H5, H7 and H9 subtypes, and the influenza A virus H3 subtype is preferably H3N2, but is not limited thereto.

In the therapeutic method of the present invention, any therapeutic agent known to those skilled in the art may be administered together with the binding molecule of the present invention.

In the therapeutic method of the present invention, the disease caused by influenza A virus may be any one selected from the group consisting of a new strain of flu, pandemic flu and seasonal flu, but is not limited thereto.

In the therapeutic method of the present invention, the dose of the binding molecule having neutralizing activity against influenza A virus may be adjusted to provide the optimum response. The dose is, for example, 0.01-200 mg/kg, preferably 0.1-150 mg/kg, and more preferably 1-100 mg/kg, but is not limited thereto. Several divided doses may be administered daily, or the dose may be proportionally reduced or increased as indicated by the exigencies of an individual's situation. The mode of administration is not limited in the present invention and can be decided by the attending physician.

In the therapeutic method of the present invention, the routes of administration of the binding molecule having neutralizing activity against influenza A virus can be divided into oral and parenteral administration routes. The preferred administration route is an intravenous route, but is not limited thereto.

The present invention also provides a method for prevention of a disease caused by influenza A virus, the method comprising administering to a subject a therapeutically effective amount of the inventive binding molecule having neutralizing activity against influenza A virus.

In the preventive method of the present invention, any preventive agent known to those skilled in the art may be administered together with the binding molecule of the present invention.

In the preventive method of the present invention, the dose of the binding molecule having neutralizing activity against influenza A virus may be adjusted to provide the optimum response. The dose is, for example, 0.01-200 mg/kg, preferably 0.1-150 mg/kg, and more preferably 1-100 mg/kg, but is not limited thereto. Several divided doses may be administered daily, or the dose may be proportionally reduced or increased as indicated by the exigencies of an individual's situation. The mode of administration is not limited in the present invention and can be decided by the attending physician.

In the preventive method of the present invention, the routes of administration of the binding molecule having neutralizing activity against influenza A virus can be divided into oral and parenteral administration routes. The preferred administration route is an intravenous route, but is not limited thereto.

The present invention also provides a method for diagnosis of influenza A virus infection of a patient, the method comprising the steps of: 1) bringing a sample into contact with the inventive binding molecule having neutralizing activity against influenza A virus; and 2) detecting a reaction between the binding molecule and the sample. In addition, the present invention also provides a method for diagnosis of influenza A virus infection of a patient, the method comprising the steps of: 1) bringing a sample into contact with the diagnostic composition of the present invention; and 2) detecting a reaction between the binding molecule and the sample.

In the diagnostic method of the present invention, the influenza A virus is preferably any one selected from the group consisting of H1, H3, H5, H7 and H9 subtypes, and the influenza A virus H3 subtype is preferably H3N2, but is not limited thereto.

In the diagnostic method of the present invention, the binding molecule of the present invention may, if necessary, be linked with a tag for diagnosis and detection according to any method known to those skilled in the art.

In the diagnostic method of the present invention, the sample is preferably any one selected from the group consisting of phlegm, spittle, blood, lung cell, lung tissue mucus, respiratory tissue and salvia, but is not limited thereto. The sample can be prepared according to any conventional method known to those skilled in the art.

In the diagnostic method of the present invention, the method for detecting the reaction may be one selected from the group consisting of homogeneous and heterogeneous binding immunoassays, such as radio-immunoassays (RIA), enzyme-linked immunosorbent assay (ELISA), immuno-fluorescence, immunocytochemistry, FACS, BIACORE and Western blot analyses, but is not limited thereto, and any detection method known to those skilled in the art may be used in the present invention.

The present invention also provides a kit for diagnosis of influenza A virus, the kit comprising: 1) the inventive binding molecule having neutralizing activity against influenza A virus; and 2) a container.

In addition, the present invention provides a kit for diagnosis of influenza A virus, the kit comprising: 1) the inventive composition for diagnosis of influenza A virus; and 2) a container.

In the diagnostic kit of the present invention, the influenza A virus is preferably any one selected from the group consisting of H1, H3, H5, H7 and H9 subtypes, and the influenza A virus H3 subtype is preferably H3N2, but is not limited thereto.

In the diagnostic kit of the present invention, the container 2) comprises a solid support. The binding molecule of the present invention can be attached to a solid support, and this solid support may be porous or nonporous, planar or nonplanar.

Example 1

Isolation of PBMC from Blood of Patients Who Recovered from Flu

A recovered patient group consisted of patient volunteers who were 2-4 weeks after confirmation of new flu infections. The volunteers were confirmed to have no influenza virus (H1N1) in their blood and had an antibody against the new influenza virus. This study was performed under the approval of the Institutional Review Board (IRB). This patients group had the following characteristics: (1) the patients were not vaccinated against seasonal flu; (2) the patients were negative for other infectious viruses, that is, HBsAg, and were negative for anti-HCV antibody and anti-HIV antibody; (3) the patient's plasma was negative for RT-PCR for the influenza virus H1N1 subtype; (4) the patient's serum showed a titer of 1:160 or higher in ELISA assays for the monomeric HA(H1N1) of the influenza A virus H1N1 subtype. About 100 ml of whole blood was collected from the volunteers, and peripheral blood mononuclear cells (PBMCs) were isolated from the collected blood using LYMPHOPREP™ density gradient medium (Axis-Shield, Norway, 1114545), The isolated PBMCs were washed three times with phosphate-buffered saline, suspended in KM banker H freezing medium (Cosmobio, Japan, KOJ-16092010) at a concentration of $2 \times 10^7$ cells/ml, and stored in a nitrogen tank.

Example 2

Primary Screening of Monoclonal Antibodies

B cells secreting antigen-specific antibodies were screened using the method described by Jin et al. Win A. et al., 2009. Nat. Med. 15, 1088-1092). Briefly, the PBMCs isolated in Example 1 were added to each well of a prepared microarray chip at a density of one cell/well. Antibodies secreted from the single cells were confirmed by the pre-coated anti-human IgG antibody. Whether the screened antibody-secreting cells secreted HA-binding antibodies was examined using the labeled HA antigen. The complete sequences of the heavy-chain and light-chain genes of the antibodies from the individual antibody-secreting cells were obtained by a reverse transcription-polymerase chain reaction (RT-PCR). The obtained heavy-chain and light-chain DNAs were inserted into PCDNA™ 3.1(+) expression vectors (Invitrogen, USA, V790-20) to prepare expression vectors that produce each of the heavy chain and light chain of the antibodies. The prepared expression vectors were co-transfected into CHO cells. Then, using the antibodies derived from the transfected CHO cells, 82 antibodies binding to HA were primarily selected by the HA-ELISA method described in Example 3 below. Herein, all the antibodies showing a reaction with HA were primarily screened without serially diluting the antibody samples.

Example 3

Verification of the Ability of Monoclonal Antibodies to Bind to HA

In order to secondarily screen monoclonal antibodies, which have a high ability to bind to the HA of H3N2 influenza virus, from the 82 primarily screened antibodies, HA-ELISA was performed using the subunit (HA1) of monomeric HA and trimeric HA. A recombinant monomeric HA1 subunit (11056-V08H1) from influenza A virus was purchased from Sino Biological Inc. (China). The purchased HA1 subunit consisted of the N-terminal fragment (Met1-Arg345) of the HA comprising polyhistidine residues at the C-terminus and was derived from transfected human cells. Recombinant trimeric HA (FR-61) was provided by IRR (Influenza Reagent Resource, USA). The trimeric HA comprised a thrombin cleavage site at the C-terminus, a trimerizing domain (foldon) and six histidine residues and was produced using a baculovirus system.

The reactivity of the antibody with the HA antigen was measured by ELISA using the HA and the antibody. Specifically, 50 µl of trimeric HA antigen (250 ng/ml) was first adsorbed onto each well of a 96 well microtiter plate (Nunc, Denmark, 449824). The plate was blocked with phosphate-buffered saline (Teknova, USA, D5120) containing 1% bovine serum albumin (BSA), and then a 3-fold serially diluted antibody sample (starting concentration: 1 µg/ml) was added to each well of the plate. Next, the plate was incubated at room temperature for 1 hour, and then treated with peroxidase labeled goat anti-human gamma antibody (Zymed, USA, 62.8420). After incubation for 1 hour at room temperature, the plate was incubated with tetramethylbenzydine (TUE; Sigma-Aldrich, USA, T0440), and the incubation was stopped by adding 1N HCl. The absorbance at 450/570 nm was measured using a plate reader (SPECTRA-MAX™ plus 384, Molecular Device), and the antigen-antibody reactivity was graphically expressed using Graphpad prism program (GraphPad Software inc. USA).

Most of the antibodies did not bind to the HA of H3N2, but as shown in FIG. 1, the CT129, CT135, CT147, CT149, CT164 and CT166 antibodies showed high binding affinities. Particularly, these antibodies did easily bind to the trimeric HA, but did not bind to the HA1 subunit. This suggests that the screened antibodies do not bind to the epitope of previously known HA1, but have the ability to bind only to the boundary between the HA1 and HA2 segments, or to HA2 or to HA with a normal conformation.

On the basis of the results shown in FIG. 1, from the 82 primarily screened antibodies, 6 antibodies (CT129, CT135, CT147, CT149, CT164 and CT166 antibodies) showing high binding affinities for the trimeric HA of H3N2 influenza virus were secondarily selected. In order to increase the expression levels of the secondarily selected antibodies, these antibody genes were recloned from the pcDNA vectors into MarEx expression vectors (constructed and patented by Celltrion, Inc.) in the following manner. After recloning, the MarEx expression vectors containing the antibody genes were used to produce antibodies required for a microneutralization test (MN test) and haemagglutination inhibition test (HI test).

Figure 2:
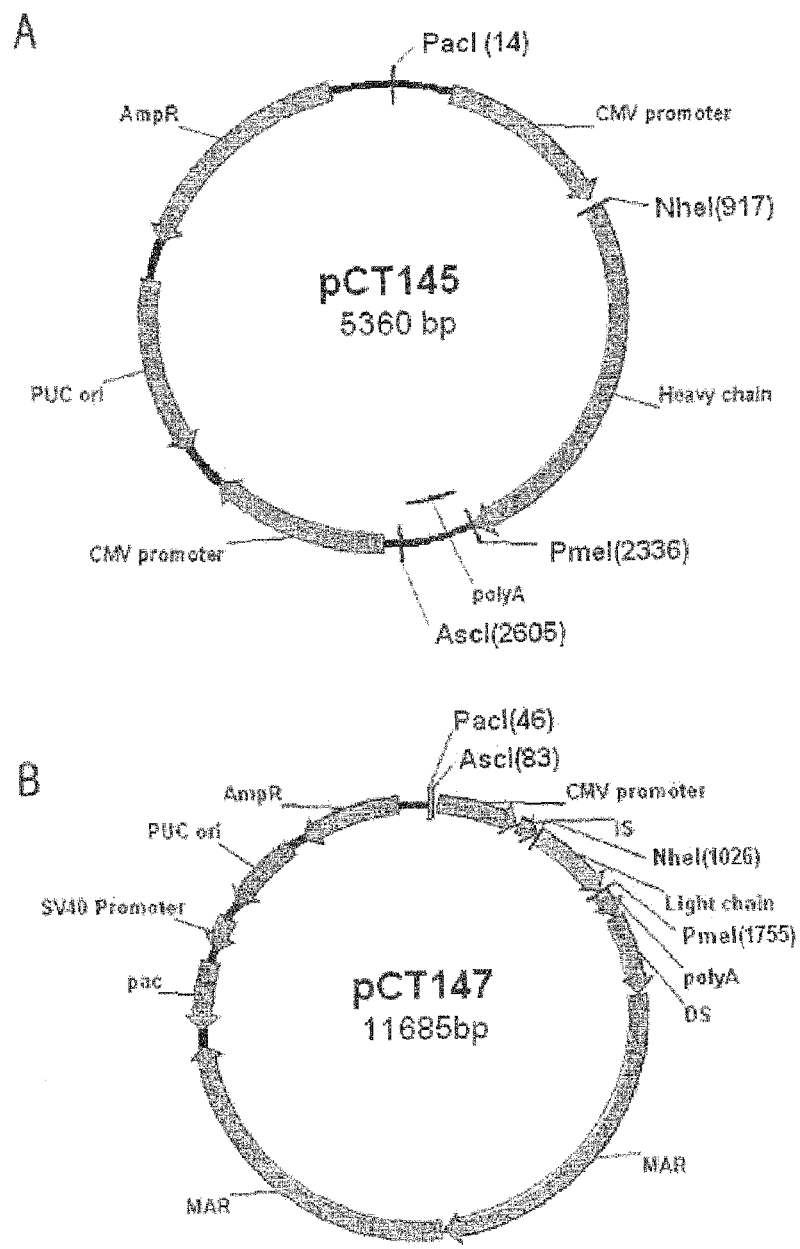
Figure 3:
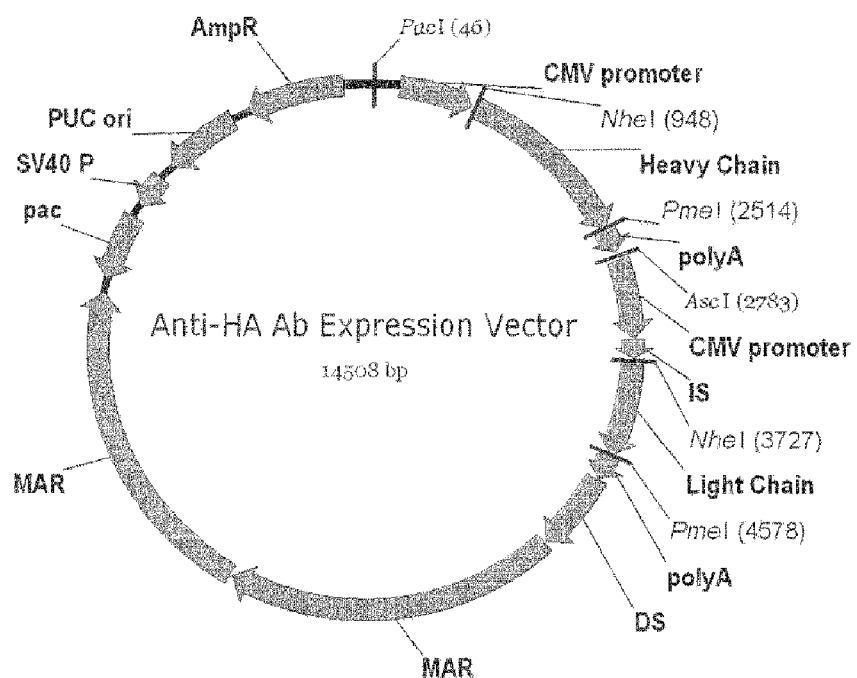

The original PCDNA™ vectors containing each of the heavy chain genes and light-chain genes of the six secondarily selected antibodies were treated with the restriction enzymes NheI and PmeI to obtain heavy-chain genes and light-chain genes. The obtained heavy-chain genes and light-chain genes were respectively inserted into pCT145 vectors and pCT147 vectors, which had been treated with the same restriction enzymes. The pCT145 and pCT147 vectors were constructed by Celltrion, Inc., in order to clone the heavy chain and the light chain of each of the antibodies, respectively (FIG. 2). Next, in order to construct expression vectors containing a heavy-chain transcription unit (promoter-heavy chain gene-poly A) together with a light-chain transcription unit (promoter-light chain gene-poly A), the pCT145 vectors containing the heavy-chain genes were treated with the restriction enzymes PacI and AscI to obtain heavy-chain transcription units, and then the pCT147 vectors containing the light-chain genes were treated with the same restriction enzymes, and then the heavy-chain transcription units were inserted therein. Then, vectors containing both the heavy-chain transcription unit and the light-chain transcription unit were screened using restriction enzymes (FIG. 3). The screened vectors were extracted using an ENDOFREE® plasmid maxi kit (QIAGEN, Germany, 12362), and the nucleotide sequences of portions of the extracted DNA samples were analyzed, thereby determining the nucleotide sequences of the antibodies.

Next, the DNA of the extracted antibodies was transfected into a suspension culture of an F2N cell line (prepared by Celltrion, Inc., Korea), thereby preparing a transient cell line producing monoclonal antibodies. The transfection was performed in the following manner. Transient transfection of the cells was carried out using the cationic polymer of FREE STYLE™ Max (Invitrogen, USA, 16447-100) according to the manufacturer's instruction. On the day before transfection, F2N cells cultured in EX-CELL® 293 serum-free media (SAFC, UK, 14571C; hereinafter referred to as "EX-CELL® 293 media") were centrifuged and suspended at a cell concentration of $1 \times 10^6$ cells/ml in modified EX-CELLO® 293 medium (SAFC, UK, 65237; made to order), and 80 ml of the cell suspension was seeded into a 250 ml Erlenmeyer flask, or 200 ml of the cell suspension was seeded into a 1-liter Erlenmeyer flask. On the day of transfection, in the case in which 80 ml of the cell suspension was seeded, each of 100 µg of a monoclonal antibody-encoding DNA and 100 µl of FREESTYLE™ Max reagent was diluted to a volume of 1.6 ml using OPTIPRO™ SFM II medium, followed by gentle stirring. In the case in which 200 ml of the cell suspension was seeded, each of 250 µg of DNA and 250 µg FREESTYLE™ Max reagent was diluted to a volume of 4 ml using OPTIPRO™ SFM II medium, followed by gentle stirring. Immediately after the stirring process, the solution containing FREESTYLE™ Max reagent diluted therein was mixed with the solution containing DNA diluted therein, and the mixed solution was incubated at room temperature for 19 minutes. During incubation at room temperature for 19 minutes, the seeded F2N cells were diluted to a cell concentration of $0.8 \times 10^6$ cells using fresh modified EX-CELL® 293 medium. After incubation for 19 minutes; the F2N cells were treated and transfected with the mixed solution containing DNA and FREESTYLE™ Max reagent. On the day after transfection, the same amount of EX-CELL® 293 medium was added to the transfected cells, which were then incubated for 7-8 days, thereby producing monoclonal antibodies.

Example 4

Examination of In Vitro Neutralizing Activity Against Viruses

The six antibodies screened in HA-ELISA were subjected to a microneutralization (MN) test in order to examine their neutralizing activity against various influenza viruses.

Example 4-1

Culture of MDCK Cell Line and Determination of Virus Concentration

As the Madin-Darby canine kidney (MDCK) cell line, the London line (MDCK-L) was used. The MDCK cell line was cultured in a 5% $CO_2$ humidified incubator at 37° C. using a DMEM medium (Gibco, USA, 11965) containing 10% FBS (Atlas Biologicals, USA, F0500A), 1× pecinillin/streptomycin (Gibco, USA, 15140), 25 mM HEPES (Gibco, USA, 15630) and 2 mM L-glutamine (Gibco, USA, 25030).

Virus concentration was quantified by a cell-based ELISA method to determine the median tissue culture infective dose (TCID$_{50}$). The determination of virus concentration was performed in the following manner. First, a virus stock was serially diluted 10-fold with a virus diluent [DMEM (Gibco, USA), 3% BSA (Gibco, USA, 15260), 1× pecinillin/streptomycin (Gibco, USA), and 25 mM HEPES (Gibco, USA)], and 100 µl of the diluted virus was added to each well of a 96-well plate. As a negative control, a virus diluent containing no virus was used. Then, the MDCK cell line that was being cultured was separated from the culture incubator by treatment with trypsin, and then treated with MDCK culture medium to neutralize the trypsin. Next, the cell pellets were washed twice with phosphate-buffered saline, and then diluted with a virus diluent to a cell concentration of 5×10$^5$ cells/ml. 3-4 mg/ml of TPCK-trypsin (Sigma, USA) was added to the 96-well plate containing the virus, and then immediately, 1000 the MDCK cell line was added to each well of the plate and incubated in a 5% CO$_2$ humidified incubator at 37° C. for 20 hours. The incubated plate was washed once with phosphate buffered saline, and then 200 µl of a mixed solution of cold acetone: phosphate buffered saline (PBS) (80:20) was added to each well of the plate. Next, the cells were fixed for 8 minutes, and the plate was dried at room temperature for 20 minutes. Each well of the plate was washed twice with 200 µl of phosphate buffered saline. Biotinylated anti-nuclear protein (NP) monoclonal antibody (Milipore, USA, MAB8257B) was diluted 2,000-fold with 1% BSA-containing phosphate buffered saline (0.1% Tween 20), and 100 µl of the dilution was added to each well of the plate and incubated at room temperature for 1 hour. The plate was washed three times with 200 µl/well of phosphate buffered saline, and then 100 µl of a 20,000-fold dilution of streptavidin-HRP-conjugated antibody in 1% BSA-containing phosphate buffered saline was added to each well of the plate and incubated at room pressure for 1 hour. After washing the plate four times with phosphate buffered saline, 100 µl of OPD solution (Sigma, USA, P8287) was added to each well of the plate, and the plate was developed at room temperature for 10 minutes and treated with 50 µl/well of 3M HCl to stop the color development, after which the OD$_{490}$ of each well was measured. Based on the measured OD$_{490}$, TCID$_{50}$ was calculated using the method of Reed & Muench (The American 1938).

Example 4-2

MN Assay

Each antibody was diluted with a virus diluent to a concentration of 10 µg/ml. From this initial concentration, the antibody dilution was serially diluted 2-fold with a virus diluent, and 50 µl of each of the dilutions was added to each well of a 96-well plate. Also, 50 µl of viruses were added to each well of the plate at a concentration corresponding to 100 TCID$_{50}$ and were incubated in a 5% CO$_2$ humidified incubator at 37° C. for 1 hour. Next, 3-4 µg/ml of TPCK-trypsin (Sigma, USA, T1426) was added to each well, and 100 µl of the treated MDCK cells were added to each well, followed by incubation in a 5% CO$_2$ humidified incubator at 37° C. for 20 hours. After incubation for 20 hours, an MN assay was carried out according to the same method as the virus quantification method described in Example 4-1, thereby determining the OD$_{490}$ value of each well. The wells showing OD$_{490}$ values higher than that of the well introduced only with the cells was determined to be infected with viruses. Among OD$_{490}$ values for each antibody at which no virus antigen was detected, the lowest concentration (µg/ml) of the antibody is shown in Table 1 below, and the lower concentration of the antibody means the higher neutralizing activity against virus.

TABLE 1

Results of Microneutralization assay (MN assay) carried out using screened antibodies and various types of H3N2 viruses

| mAb ID | A/Wisconsin/67/05 | A/Hong Kong/68 | A/Brisbane/10/07 |
|---|---|---|---|
| CT129 | >10 µg/ml | >10 µg/mL | >10 µg/mL |
| CT135 | >10 µg/ml | 5 µg/mL | 5 µg/mL |
| CT147 | 2.5 µg/mL | 2.5 µg/mL | 0.625 µg/mL |
| CT149 | 1.25 µg/mL | 2.5 µg/mL | 1.25 µg/mL |
| CT164 | 2.5 µg/mL | 1.25 µg/mL | 0.625 µg/mL |
| CT166 | 5 µg/mL | 2.5 µg/mL | 1.25 µg/mL |

*Unit: µg/ml

As can be seen from the results of MN assays of six candidate antibodies against H3 subtype influenza viruses, the CT129 antibody showed high binding affinity in HA-ELISA, but did not show neutralizing activity against the three types of viruses used in the assays. The CT135 antibody showed neutralizing activity against two types of H3N2 viruses (A/Hong Kong/68 and A/Brisbane/10/07), and the CT147, CT149, CT164 and CT166 antibodies showed neutralizing activity against three kinds of H3N2 viruses (A/Wisconsin/67/05, A/Hong Kong/68 and A/Brisbane/10/07).

Among the above-mentioned antibodies, the CT149 antibody was selected, and its neutralizing activities against various types of influenza viruses were analyzed by an MN assay (Table 2).

TABLE 2

Results of microneutralization assay (MN assay) carried out using selected antibody and various types of viruses

| Subtype | strains | MN titer (µg/mL) |
|---|---|---|
| H1N1 | A/OH/07/2009 | 10 µg/mL |
| H2N2 | A/Ann Arbor/6/60, CA | >20 µg/mL |
| H5N1 | A/Vietnam/1203/04 x PR8 | 2.5 µg/mL |
| H7N2 | A/turkey/Virginia/02 x PR8 | 10 µg/mL |
| H9N2 | A/Green-winged teal/209/TX/2009 | 0.156 µg/mL |
| H9N2 | A/ck/HK/G9/97 x PR8 | 0.625 µg/mL |
| H3N2 | A/Beijing/353/89-X109 | 0.156 µg/mL |
| H3N2 | A/Beijing/32/92-R-H3 | 0.078 µg/mL |
| H3N2 | A/Johannesburg/33/94 R-H3 | 0.625 µg/mL |
| H3N2 | A/Nanchang/933/95 | 0.625 µg/mL |
| H3N2 | A/Sydney/5/97 | 0.625 µg/mL |
| H3N2 | A/Panama/2007/99 | 0.312 µg/mL |
| H3N2 | Wyomin/3/03.rg | 5 µg/mL |
| H3N2 | A/Brisbane/10/07 | 0.625 µg/mL |

As can be seen in Table 2 above, the CT149 antibody showed neutralizing activity against the H1N1, H5N1, H7N2, H9N2 and H3N2 subtype influenza viruses used in the MN assay.

Example 5

Examination of the Ability of Antibody to Inhibit Hemagglutination Reaction Caused by Viruses An antibody was serially diluted 2-fold on a V-bottom 96-well plate, and viruses having 4-fold HA units were added to and mixed with the antibody. Next, the plate was incubated at room temperature for 30 minutes, and then 1% avian red blood cells were added to each well of the plate. The hemagglutination inhibition end point was determined as the lowest antibody concentration at which no hemagglutination reaction was observed.

As a result, all the antibodies tested did not inhibit hemagglutination for the H3N2 subtype virus (A/Brisbane/10/07), used in the test, even at high concentrations (>20 µg/ml) (Table 3).

TABLE 3

Results of hemagglutination-inhibition test for screened antibodies against H3N2 subtype virus

| mAb ID | A/Brisbane/10/07 |
|---|---|
| CT129 | >20 µg/ml |
| CT135 | >20 µg/ml |
| CT147 | >20 µg/ml |
| CT149 | >20 µg/ml |
| CT164 | >20 µg/ml |
| CT166 | >20 µg/ml |

Example 6

Examination of Preventive and Therapeutic Effects of Antibody Against Influenza Viruses by Animal Experiment Example 6-1

Examination of Preventive and Therapeutic Effects of Antibody Against Influenza Viruses in Mice In order to examine whether the CT149 antibody has preventive and therapeutic effects against H3N2 virus in mice, the following experiment was carried out. Each group consisting of five mice was intranasally infected with 10 $LD_{50}$ of A/Hong Kong/68 virus. The CT149 antibody was administered to mice by intraperitoneal injection in an amount of 10 or 20 mg/kg at 24 hours before viral infection or at 24 hours or 48 hours after viral infection.

Figure 4:
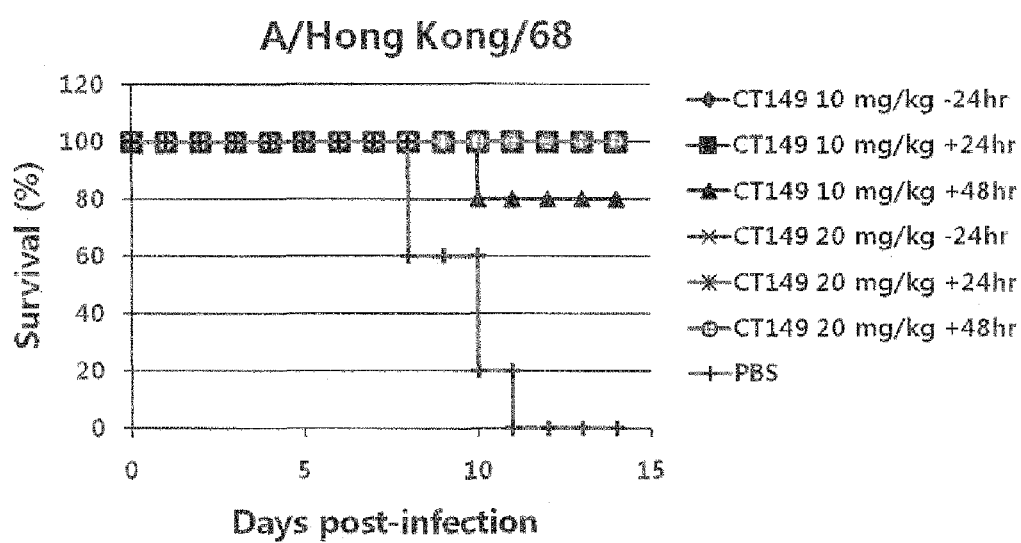

As a result, as shown in FIG. 4, in the case of the negative control group, all the mice of the negative control group died before 11 days after viral infection, whereas in the case of the group injected with 10 mg/kg or 20 mg/kg of the CT149 antibody 24 hours or 48 hours after viral infection, all the mice survived, suggesting that the CT149 antibody has a preventive effect against viral infection. In the case in which the CT149 antibody was injected after viral infection in order to confirm the therapeutic effect of the antibody, when the mice were injected with 10 mg/kg of the antibody 48 hours after viral infection, 20% of the mice died, and when the mice were injected with 10 mg/kg of the antibody 24 hours after viral infection or with 20 mg/kg of the antibody 48 hours after viral infection, all the mice survived, suggesting that the CT149 antibody has a therapeutic effect against viral infection.

Example 6-2

Examination of Therapeutic Effect of Antibody Against Influenza Virus in Ferrets Ferrets shows sensitivities and symptoms similar to those of humans for influenza virus, and thus are frequently used in studies on influenza virus. Thus, the following experiment was carried out using ferrets in order to examine whether the CT149 antibody has therapeutic effects against H3N2 and H5N1 viruses.

Each test group consisted of 9 ferrets. The nasal cavity and organ of each ferret were infected with $1 \times 10^6$ $EID_{50}$/ml of H3N2 (A/Hongkong/68) influenza virus or $1 \times 10^2$ $EID_{50}$/ml of H5N1 (A/Vietnam/1203/04) influenza virus. One day after viral infection, each ferret was injected intravenously once with 30 mg/kg of the negative control CT-P6 antibody (regardless of influenza virus) or 15 mg/kg or 30 mg/kg of the CT149 antibody or was intravenously with 30 mg/kg of the CT149 antibody once a day for 3 days.

1, 3, 5, 7 and 9 days after viral infection, the nasal wash was collected from the ferrets of each test group using 1 ml of antibiotic-containing PBS. 3, 5 and 9 after viral infection, 3 ferrets of each test group were sacrificed, and the lung tissue was extracted and the viral concentration thereof was measured using fertile eggs. To perform a virus titration test using fertile eggs, the nasal wash was centrifuged, and 1 g of the ferret lung tissue was added to 1 ml of antibiotic-containing PBS, disrupted and centrifuged. Each of the supernatants was serially diluted with 10-fold with antibiotic-containing PBS. 10-13-day-old fertile eggs were infected with the diluted supernatant and incubated for 48 hours. Then, 50 µl of the allantoic fluid collected from the eggs was mixed with the same amount of 0.5% red blood cells, and the mixture was incubated for 30 minutes, and then titrated with virus by agglutination of blood.

Figure 5:
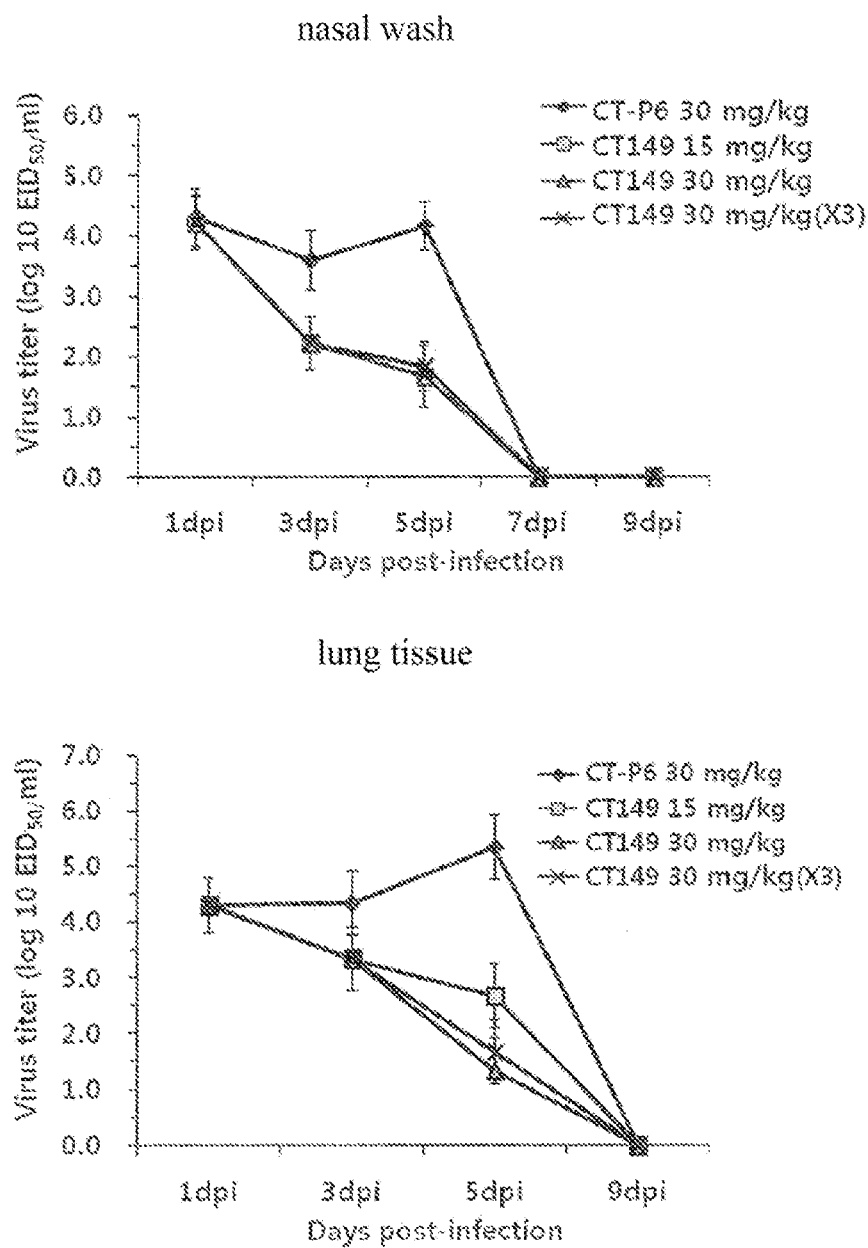

The viral titers in the test animals (ferrets) administered with the negative control (CT-P6) and CT149 at 24 hours after infection with H3N2 (A/Hongkong/68) influenza virus were measured. As a result, in the case of the negative control group, a viral titer of about log 4 $EID_{50}$/ml or higher was observed one day after viral infection, and the viral titers in the nasal wash and the lung tissue were kept or increased until 5 days after infection. However, 7 days after viral infection, no virus was detected in the control group. The group administered with CT149 showed a viral titer similar to that of the negative control group at one day after viral infection, but the viral titer in the CT149-treated group started to decrease after 3 days, and no virus was detected in the CT149-treated group at day 9, indicating that the virus in the CT149-treated group was removed fast. Particularly, the viral titer in the lung tissue decreased faster as the amount of antibody administered increased (FIG. 5).

Figure 6:
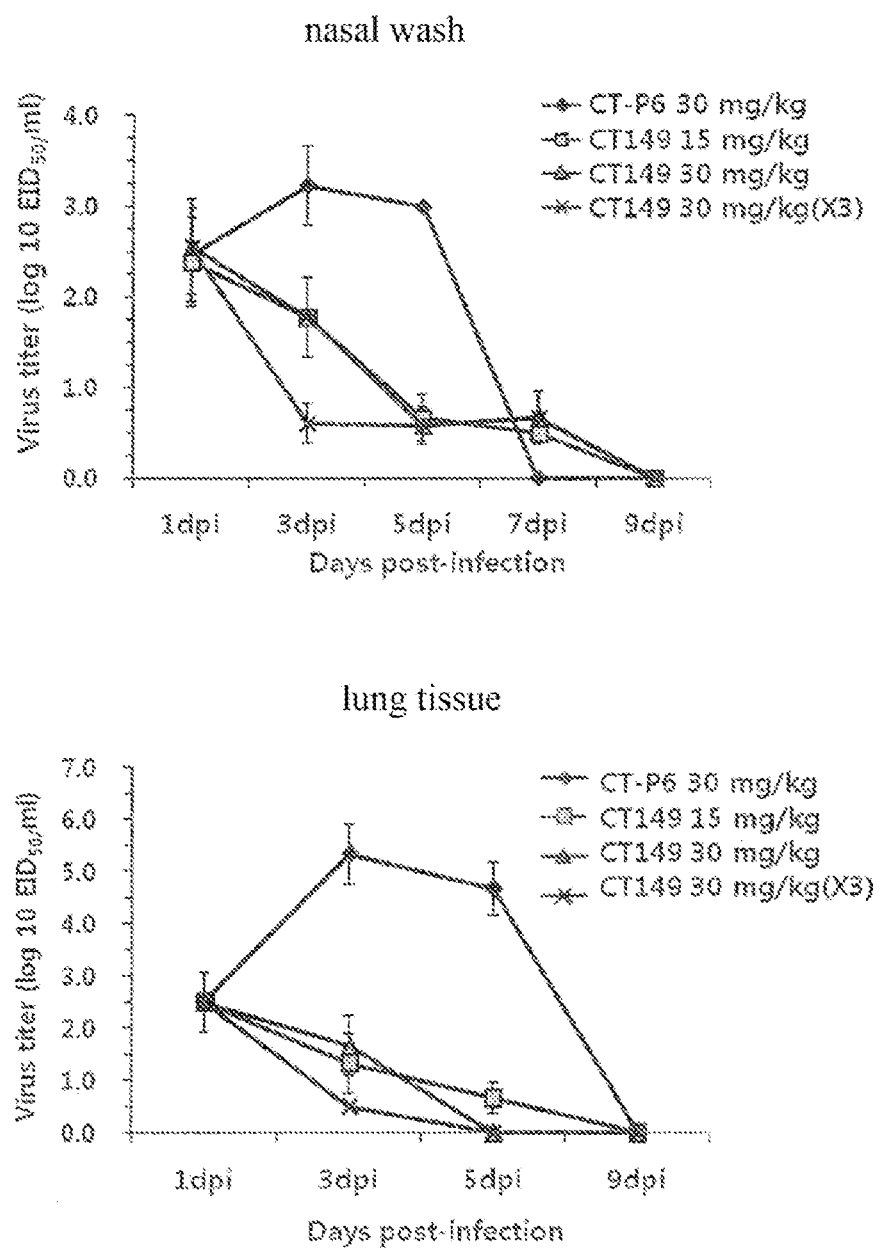

The viral titers in the test animals (ferrets) administered with the negative control (CT-P6) and CT149 at 24 hours after infection with H5N1 (A/Vietnam/1203/04) influenza virus were measured. As a result, in the case of the negative control group, a viral titer of about log 2.4 $EID_{50}$/ml or higher was observed one day after viral infection, and the viral titers in the nasal wash and the lung tissue were increased until 5 days after viral infection. At 5 days after viral infection, only one of six ferrets in the control group survived, and thus the virus titer in the nasal wash was measured in only one ferret at 5 days. At 9 days after viral infection, all the ferrets in the control group already died, and thus the viral titer could not be measured. In the group administered with CT149, the virus titer started to decrease from 3 days after viral infection, and no virus was detected at 9 days, indicating that the virus was removed fast. Also, the viral titer in the group to administered with CT149 decreased faster as the amount of antibody administered increased. In addition, in the group administered once with 15 mg/kg of CT149, only one ferret died at 7 days after viral infection, suggesting that CT149 has a therapeutic effect against influenza virus (FIG. 6).

The invention claimed is:
1. A binding molecule comprising:
   (a) a binding molecule composed of a light chain comprising, as determined according to the Kabat method, a CDR1 region comprising a polypeptide encoded by a polynucleotide sequence set forth in SEQ ID NO: 18, a CDR2 region comprising a polypeptide encoded by a polynucleotide sequence set forth in SEQ ID NO: 19, and a CDR3 region comprising a polypeptide encoded by a polynucleotide sequence set forth in SEQ ID NO: 20, and a heavy chain comprising, as determined according to the Kabat method, a CDR1 region com- prising a polypeptide encoded by a polynucleotide sequence set forth in SEQ ID NO: 21, a CDR2 region comprising a polypeptide encoded by a polynucleotide sequence set forth in SEQ ID NO: 22, and a CDR3 region comprising a polypeptide encoded by a polynucleotide sequence set forth in SEQ ID NO: 23;

(b) a binding molecule composed of a light chain comprising, as determined according to the Kabat method, a CDR1 region comprising a polypeptide encoded by a polynucleotide sequence set forth in SEQ ID NO: 24, a CDR2 region comprising a polypeptide encoded by a polynucleotide sequence set forth in SEQ ID NO: 25, and a CDR3 region comprising a polypeptide encoded by a polynucleotide sequence set forth in SEQ ID NO: 26, and a heavy chain comprising, as determined according to the Kabat method, a CDR1 region comprising a polypeptide encoded by a polynucleotide sequence set forth in SEQ ID NO: 27, a CDR2 region comprising a polypeptide encoded by a polynucleotide sequence set forth in SEQ ID NO: 28, and a CDR3 region comprising a polypeptide encoded by a polynucleotide sequence set forth in SEQ ID NO: 29;

(c) a binding molecule composed of a light chain comprising, as determined according to the Kabat method, a CDR1 region comprising a polypeptide encoded by a polynucleotide sequence set forth in SEQ ID NO: 30, a CDR2 region comprising a polypeptide encoded by a polynucleotide sequence set forth in SEQ ID NO: 25, and a CDR3 region comprising a polypeptide encoded by a polynucleotide sequence set forth in SEQ ID NO: 26, and a heavy chain comprising, as determined according to the Kabat method, a CDR1 region comprising a polypeptide encoded by a polynucleotide sequence set forth in SEQ ID NO: 31, a CDR2 region comprising a polypeptide encoded by a polynucleotide sequence set forth in SEQ ID NO: 32, and a CDR3 region comprising a polypeptide encoded by a polynucleotide sequence set forth in SEQ ID NO: 33; or (d) a binding molecule composed of a light chain comprising, as determined according to the Kabat method, a CDR1 region comprising a polypeptide encoded by a polynucleotide sequence set forth in SEQ ID NO: 34, a CDR2 region comprising a polypeptide encoded by a polynucleotide sequence set forth in SEQ ID NO: 35, and a CDR3 region comprising a polypeptide encoded by a polynucleotide sequence set forth in SEQ ID NO: 26, and a heavy chain comprising, as determined according to the Kabat method, a CDR1 region comprising a polypeptide encoded by a polynucleotide sequence set forth in SEQ ID NO: 31, a CDR2 region comprising a polypeptide encoded by a polynucleotide sequence set forth in SEQ ID NO: 36, and a CDR3 region comprising a polypeptide encoded by a polynucleotide sequence set forth in SEQ ID NO: 29.

2. The binding molecule of claim 1, wherein the binding molecule is composed of a light chain comprising a polypeptide encoded by polynucleotide sequence set forth in SEQ ID NO: 45, and a heavy chain comprising a polypeptide encoded by polynucleotide sequence set forth in SEQ ID NO: 46.

3. The binding molecule of claim 1, wherein the binding molecule is composed of a light chain comprising a polypeptide encoded by polynucleotide sequence set forth in SEQ ID NO: 47, and a heavy chain comprising a polypeptide encoded by polynucleotide sequence set forth in SEQ ID NO: 48.

4. The binding molecule of claim 1, wherein the binding molecule is composed of a light chain comprising a polypeptide encoded by polynucleotide sequence set forth in SEQ ID NO: 49, and a heavy chain comprising a polypeptide encoded by polynucleotide sequence set forth in SEQ ID NO: 50.

5. The binding molecule of claim 1, wherein the binding molecule is composed of a light chain comprising a polypeptide encoded by polynucleotide sequence set forth in SEQ ID NO: 51, and a heavy chain comprising a polypeptide encoded by polynucleotide sequence set forth in SEQ ID NO: 52.

6. A composition for diagnosis of influenza A virus, the composition comprising a conjugate comprising a tag linked to a binding molecule having neutralizing activity against influenza A virus, wherein the binding molecule is:

(a) a binding molecule composed of a light chain comprising, as determined according to the Kabat method, a CDR1 region set forth in SEQ ID NO: 1, a CDR2 region set forth in SEQ ID NO: 2, and a CDR3 region set forth in SEQ ID NO: 3, and a heavy chain comprising, as determined according to the Kabat method, a CDR1 region set forth in SEQ ID NO: 4, a CDR2 region set forth in SEQ ID NO: 5, and a CDR3 region set forth in SEQ ID NO: 6;

(b) a binding molecule composed of a light chain comprising, as determined according to the Kabat method, a CDR1 region set forth in SEQ ID NO: 7, a CDR2 region set forth in SEQ ID NO: 8, and a CDR3 region set forth in SEQ ID NO: 9, and a heavy chain comprising, as determined according to the Kabat method, a CDR1 region set forth in SEQ ID NO: 10, a CDR2 region set forth in SEQ ID NO: 11, and a CDR3 region set forth in SEQ ID NO: 12;

(c) a binding molecule composed of a light chain comprising, as determined according to the Kabat method, a CDR1 region set forth in SEQ ID NO: 13, a CDR2 region set forth in SEQ ID NO: 8, and a CDR3 region set forth in SEQ ID NO: 9, and a heavy chain comprising, as determined according to the Kabat method, a CDR1 region set forth in SEQ ID NO: 10, a CDR2 region set forth in SEQ ID NO: 14, and a CDR3 region set forth in SEQ ID NO: 6; or (d) a binding molecule composed of a light chain comprising, as determined according to the Kabat method, a CDR1 region set forth in SEQ ID NO: 15, a CDR2 region set forth in SEQ ID NO: 16, and a CDR3 region set forth in SEQ ID NO: 9, and a heavy chain comprising, as determined according to the Kabat method, a CDR1 region set forth in SEQ ID NO: 10, a CDR2 region set forth in SEQ ID NO: 17, and a CDR3 region set forth in SEQ ID NO: 12.

7. The composition of claim 6, wherein the tag is any one selected from the group consisting of enzymes, luciferases, radioactive isotopes, and toxin.

8. The binding molecule of claim 1, wherein the binding molecule is an antibody.

9. The binding molecule of claim 8, wherein the antibody is a Fab fragment, a Fv fragment, a diabody, a chimeric antibody, a humanized antibody or a human antibody.

10. A composition comprising a binding molecule having neutralizing activity against influenza A virus according to claim 1.

11. The composition of claim 10, wherein the influenza A virus is selected from the group consisting of H1, H3, H5, H7 and H9 subtypes.

12. A composition for preventing and treating a disease caused by influenza A virus, the composition comprising a binding molecule having neutralizing activity against influenza A virus according to claim 1.

13. A kit for diagnosis of influenza A virus, comprising:
   i) a binding molecule having neutralizing activity against influenza A virus according to claim 1; and
   ii) a container.

14. The kit of claim 13, wherein the influenza A virus is selected from the group consisting of H1, H3, H5, H7 and H9 subtypes.

15. The binding molecule of claim 1, wherein the binding molecule is produced by mammalian cell culture.

16. The binding molecule of claim 15, wherein the mammalian cell culture is CHO cells, F2N cells, COS cells, BHK cells, Bowes melanoma cells, HeLa cells, 911 cells, HT1080 cells, A549 cells, HEK 293 cells, or HEK293T cells.

* * * * *

SEQUENCE LISTING

<160> NUMBER OF SEQ ID NOS: 52

<210> SEQ ID NO 1
<211> LENGTH: 12
<212> TYPE: PRT
<213> ORGANISM: Artificial Sequence
<220> FEATURE:
<223> OTHER INFORMATION: CT147_LC_CDR1

<400> SEQUENCE: 1

Arg Ala Ser Arg Arg Val Gly Ser Thr Tyr Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CT147_LC_CDR2

<400> SEQUENCE: 2

Gly Ala Ser Ser Arg Ala Ala
1               5

<210> SEQ ID NO 3
<211> LENGTH: 9
<212> TYPE: PRT
<213> ORGANISM: Artificial Sequence
<220> FEATURE:
<223> OTHER INFORMATION: CT147_LC_CDR3

<400> SEQUENCE: 3

Gln Gln Tyr Ala Ala Ser Pro Trp Thr
1               5

<210> SEQ ID NO 4
<211> LENGTH: 5
<212> TYPE: PRT
<213> ORGANISM: Artificial Sequence
<220> FEATURE:
<223> OTHER INFORMATION: CT147_HC_CDR1

<400> SEQUENCE: 4

Thr Tyr Gly Ile Ser
1               5

<210> SEQ ID NO 5
<211> LENGTH: 17
<212> TYPE: PRT
<213> ORGANISM: Artificial Sequence
<220> FEATURE:
<223> OTHER INFORMATION: CT147_HC_CDR2

<400> SEQUENCE: 5

Trp Ile Ser Ala Tyr Thr Gly Asn Thr Asp Tyr Ala Gln Lys Val Gln
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: CT149_CT164_HC_CDR3

<400> SEQUENCE: 6

```
Asp Lys Val Gln Gly Arg Val Glu Ala Gly Ser Gly Gly Arg His Asp
1               5                   10                  15
Tyr

<210> SEQ ID NO 7
<211> LENGTH: 12
<212> TYPE: PRT
<213> ORGANISM: Artificial Sequence
<220> FEATURE:
<223> OTHER INFORMATION: CT149_LC_CDR1

<400> SEQUENCE: 7

Arg Ala Ser His Arg Val Gly Ser Thr Tyr Ile Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: CT149_CT164_LC_CDR2

<400> SEQUENCE: 8

Gly Ala Ser Asn Arg Ala Thr
1               5

<210> SEQ ID NO 9
<211> LENGTH: 9
<212> TYPE: PRT
<213> ORGANISM: Artificial Sequence
<220> FEATURE:
<223> OTHER INFORMATION: CT149_CT164_CT166_LC_CDR3

<400> SEQUENCE: 9

Gln Gln Phe Ser Val Ser Pro Trp Thr
1               5

<210> SEQ ID NO 10
<211> LENGTH: 5
<212> TYPE: PRT
<213> ORGANISM: Artificial Sequence
<220> FEATURE:
<223> OTHER INFORMATION: CT149_CT164_CT166_HC_CDR1

<400> SEQUENCE: 10

Thr Tyr Gly Val Ser
1               5

<210> SEQ ID NO 11
<211> LENGTH: 17
<212> TYPE: PRT
<213> ORGANISM: Artificial Sequence
<220> FEATURE:
<223> OTHER INFORMATION: CT149_HC_CDR2

<400> SEQUENCE: 11

Trp Ile Ser Ala Tyr Thr Gly Ile Thr Asp Tyr Ala Gln Lys Phe Gln
1               5                   10                  15
Gly

<210> SEQ ID NO 12
<211> LENGTH: 17
<212> TYPE: PRT
<213> ORGANISM: Artificial Sequence
<220> FEATURE:
<223> OTHER INFORMATION: CT149_CT166_HC_CDR3
```

```
-continued

<400> SEQUENCE: 12

Asp Lys Val Gln Gly Arg Val Glu Val Gly Ser Gly Gly Arg His Asp
1               5                   10                  15

Tyr

<210> SEQ ID NO 13
<211> LENGTH: 12
<212> TYPE: PRT
<213> ORGANISM: Artificial Sequence
<220> FEATURE:
<223> OTHER INFORMATION: CT164_LC_CDR1

<400> SEQUENCE: 13

Arg Ala Ser His Ser Val Gly Ser Thr Tyr Ile Ala
1               5                   10

<210> SEQ ID NO 14
<211> LENGTH: 17
<212> TYPE: PRT
<213> ORGANISM: Artificial Sequence
<220> FEATURE:
<223> OTHER INFORMATION: CT164_HC_CDR2

<400> SEQUENCE: 14

Trp Ile Ser Gly Tyr Thr Gly Ile Thr Asp Tyr Ala Gln Lys Ser Gln
1               5                   10                  15

Gly

<210> SEQ ID NO 15
<211> LENGTH: 12
<212> TYPE: PRT
<213> ORGANISM: Artificial Sequence
<220> FEATURE:
<223> OTHER INFORMATION: CT166_LC_CDR1

<400> SEQUENCE: 15

Arg Ala Ser His Ser Ile Gly Ser Thr Tyr Ile Ala
1               5                   10

<210> SEQ ID NO 16
<211> LENGTH: 7
<212> TYPE: PRT
<213> ORGANISM: Artificial Sequence
<220> FEATURE:
<223> OTHER INFORMATION: CT166_LC_CDR2

<400> SEQUENCE: 16

Gly Ala Ser Asn Arg Ala Ser
1               5

<210> SEQ ID NO 17
<211> LENGTH: 17
<212> TYPE: PRT
<213> ORGANISM: Artificial Sequence
<220> FEATURE:
<223> OTHER INFORMATION: CT166_HC_CDR2

<400> SEQUENCE: 17

Trp Ile Ser Gly Tyr Thr Gly Ile Thr Asp Tyr Ala Gln Lys Phe Gln
1               5                   10                  15

Gly

<210> SEQ ID NO 18
```

<211> LENGTH: 36
<212> TYPE: DNA
<213> ORGANISM: Artificial Sequence
<220> FEATURE:
<223> OTHER INFORMATION: CT147_LC_CDR1

<400> SEQUENCE: 18
agggccagtc ggcgcgttgg cagcacctac ttagcc                36

<210> SEQ ID NO 19
<211> LENGTH: 21
<212> TYPE: DNA
<213> ORGANISM: Artificial Sequence
<220> FEATURE:
<223> OTHER INFORMATION: CT147_LC_CDR2

<400> SEQUENCE: 19
ggtgcatcca gcagggccgc t                                21

<210> SEQ ID NO 20
<211> LENGTH: 27
<212> TYPE: DNA
<213> ORGANISM: Artificial Sequence
<220> FEATURE:
<223> OTHER INFORMATION: CT147_LC_CDR3

<400> SEQUENCE: 20
cagcagtatg ctgcctcacc gtggacg                          27

<210> SEQ ID NO 21
<211> LENGTH: 15
<212> TYPE: DNA
<213> ORGANISM: Artificial Sequence
<220> FEATURE:
<223> OTHER INFORMATION: CT147_HC_CDR1

<400> SEQUENCE: 21
acctatggca tcagc                                       15

<210> SEQ ID NO 22
<211> LENGTH: 51
<212> TYPE: DNA
<213> ORGANISM: Artificial Sequence
<220> FEATURE:
<223> OTHER INFORMATION: CT147_HC_CDR2

<400> SEQUENCE: 22
tggatcagcg cttatactgg aaatacagac tatgcacaga aggtccaggg c    51

<210> SEQ ID NO 23
<211> LENGTH: 51
<212> TYPE: DNA
<213> ORGANISM: Artificial Sequence
<220> FEATURE:
<223> OTHER INFORMATION: CT147_HC_CDR3

<400> SEQUENCE: 23
gataaggtcc aggggcgcgt tgaagcggga agtgggggcc ggcatgacta c    51

<210> SEQ ID NO 24
<211> LENGTH: 36
<212> TYPE: DNA
<213> ORGANISM: Artificial Sequence
<220> FEATURE:
<223> OTHER INFORMATION: CT149_LC_CDR1

<400> SEQUENCE: 24

```
agggccagtc accgtgttgg cagcacctac atagcc                          36
```

<210> SEQ ID NO 25
<211> LENGTH: 21
<212> TYPE: DNA
<213> ORGANISM: Artificial Sequence
<220> FEATURE:
<223> OTHER INFORMATION: CT149_CT164_LC_CDR2

<400> SEQUENCE: 25

```
ggtgcatcca acagggccac t                                          21
```

<210> SEQ ID NO 26
<211> LENGTH: 27
<212> TYPE: DNA
<213> ORGANISM: Artificial Sequence
<220> FEATURE:
<223> OTHER INFORMATION: CT149_CT164_CT166_LC_CDR3

<400> SEQUENCE: 26

```
cagcagttta gtgtttcacc gtggacg                                    27
```

<210> SEQ ID NO 27
<211> LENGTH: 15
<212> TYPE: DNA
<213> ORGANISM: Artificial Sequence
<220> FEATURE:
<223> OTHER INFORMATION: CT149_HC_CDR1

<400> SEQUENCE: 27

```
acttatggag tcagt                                                 15
```

<210> SEQ ID NO 28
<211> LENGTH: 51
<212> TYPE: DNA
<213> ORGANISM: Artificial Sequence
<220> FEATURE:
<223> OTHER INFORMATION: CT149_HC_CDR2

<400> SEQUENCE: 28

```
tggatcagcg cttacactgg tatcacagac tacgcacaga gtttcaggg c           51
```

<210> SEQ ID NO 29
<211> LENGTH: 51
<212> TYPE: DNA
<213> ORGANISM: Artificial Sequence
<220> FEATURE:
<223> OTHER INFORMATION: CT149_CT166_HC_CDR3

<400> SEQUENCE: 29

```
gataaggtgc aggggcgcgt tgaagtggga tctgggggtc gtcatgacta c          51
```

<210> SEQ ID NO 30
<211> LENGTH: 36
<212> TYPE: DNA
<213> ORGANISM: Artificial Sequence
<220> FEATURE:
<223> OTHER INFORMATION: CT164_LC_CDR1

<400> SEQUENCE: 30

```
agggccagtc acagtgttgg cagcacctac atagcc                          36
```

<210> SEQ ID NO 31
<211> LENGTH: 15
<212> TYPE: DNA

<213> ORGANISM: Artificial Sequence
<220> FEATURE:
<223> OTHER INFORMATION: CT164_CT166_HC_CDR1

<400> SEQUENCE: 31
acttatggag tcagc                                                    15

<210> SEQ ID NO 32
<211> LENGTH: 51
<212> TYPE: DNA
<213> ORGANISM: Artificial Sequence
<220> FEATURE:
<223> OTHER INFORMATION: CT164_HC_CDR2

<400> SEQUENCE: 32
tggatcagcg gttatactgg tatcacagac tacgcacaga agtctcaggg c             51

<210> SEQ ID NO 33
<211> LENGTH: 51
<212> TYPE: DNA
<213> ORGANISM: Artificial Sequence
<220> FEATURE:
<223> OTHER INFORMATION: CT164_HC_CDR3

<400> SEQUENCE: 33
gacaaagtgc aggggcgcgt tgaagcggga tctgggggtc gtcacgacta c             51

<210> SEQ ID NO 34
<211> LENGTH: 36
<212> TYPE: DNA
<213> ORGANISM: Artificial Sequence
<220> FEATURE:
<223> OTHER INFORMATION: CT166_LC_CDR1

<400> SEQUENCE: 34
agggccagtc acagtattgg cagcacctac atagcc                             36

<210> SEQ ID NO 35
<211> LENGTH: 21
<212> TYPE: DNA
<213> ORGANISM: Artificial Sequence
<220> FEATURE:
<223> OTHER INFORMATION: CT166_LC_CDR2

<400> SEQUENCE: 35
ggtgcatcca acagggcctc t                                             21

<210> SEQ ID NO 36
<211> LENGTH: 51
<212> TYPE: DNA
<213> ORGANISM: Artificial Sequence
<220> FEATURE:
<223> OTHER INFORMATION: CT166_HC_CDR2

<400> SEQUENCE: 36
tggatcagcg gttacactgg tatcacagac tacgcacaga agtttcaggg c             51

<210> SEQ ID NO 37
<211> LENGTH: 215
<212> TYPE: PRT
<213> ORGANISM: Artificial Sequence
<220> FEATURE:
<223> OTHER INFORMATION: CT147_LC_Fab

<400> SEQUENCE: 37

Glu Ile Val Leu Thr Gln Ser Pro Gly Thr Leu Ser Val Ser Pro Gly

```
1               5                   10                  15
Glu Arg Ala Thr Leu Ser Cys Arg Ala Ser Arg Arg Val Gly Ser Thr
                20                  25                  30
Tyr Leu Ala Trp Tyr Gln Gln Lys Pro Gly Gln Ala Pro Arg Arg Leu
            35                  40                  45
Ile Tyr Gly Ala Ser Ser Arg Ala Gly Ile Pro Asp Arg Phe Ser
        50                  55                  60
Gly Thr Gly Ser Gly Thr Asp Phe Thr Leu Thr Ile Ser Arg Val Asp
65                  70                  75                  80
Pro Glu Asp Phe Ala Val Tyr Tyr Cys Gln Gln Tyr Ala Ala Ser Pro
                85                  90                  95
Trp Thr Phe Gly Gln Gly Thr Thr Val Glu Ile Lys Arg Thr Val Ala
            100                 105                 110
Ala Pro Ser Val Phe Ile Phe Pro Pro Ser Asp Glu Gln Leu Lys Ser
            115                 120                 125
Gly Thr Ala Ser Val Val Cys Leu Leu Asn Asn Phe Tyr Pro Arg Glu
        130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
            195                 200                 205
Ser Phe Asn Arg Gly Glu Cys
        210                 215

<210> SEQ ID NO 38
<211> LENGTH: 456
<212> TYPE: PRT
<213> ORGANISM: Artificial Sequence
<220> FEATURE:
<223> OTHER INFORMATION: CT147_HC_Fab
<220> FEATURE:
<221> NAME/KEY: UNSURE
<222> LOCATION: (219)..(219)
<223> OTHER INFORMATION: undefined residue

<400> SEQUENCE: 38

Gln Val Gln Leu Val Gln Ser Gly Gly Glu Leu Lys Lys Pro Gly Ala
1               5                   10                  15
Ser Val Arg Val Ser Cys Lys Ala Ser Gly Tyr Thr Phe Thr Thr Tyr
                20                  25                  30
Gly Ile Ser Trp Val Arg Gln Ala Pro Gly Gln Gly Leu Glu Trp Val
            35                  40                  45
Gly Trp Ile Ser Ala Tyr Thr Gly Asn Thr Asp Tyr Ala Gln Lys Val
        50                  55                  60
Gln Gly Arg Val Thr Met Thr Thr Asp Thr Ser Thr Ser Thr Ala Tyr
65                  70                  75                  80
Met Glu Leu Arg Ser Leu Thr Ser Asp Asp Thr Ala Val Tyr Tyr Cys
                85                  90                  95
Ala Arg Asp Lys Val Gln Gly Arg Val Glu Ala Gly Ser Gly Gly Arg
                100                 105                 110
His Asp Tyr Trp Gly Gln Gly Thr Leu Val Thr Val Ser Ser Ala Ser
            115                 120                 125
```

```
Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Xaa Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Gly Leu His Asn His Tyr Thr Gln Lys
        435                 440                 445

Ser Leu Ser Leu Ser Pro Gly Lys
    450                 455

<210> SEQ ID NO 39
<211> LENGTH: 215
<212> TYPE: PRT
<213> ORGANISM: Artificial Sequence
<220> FEATURE:
<223> OTHER INFORMATION: CT149_LC_Fab

<400> SEQUENCE: 39

Glu Val Val Leu Thr Gln Ser Pro Gly Thr Leu Ala Leu Pro Pro Gly
1               5                   10                  15

Glu Arg Ala Thr Leu Ser Cys Arg Ala Ser His Arg Val Gly Ser Thr
            20                  25                  30
```

Tyr Ile Ala Trp Tyr Gln Gln Lys Ser Gly Gln Ala Pro Arg Arg Leu
            35                  40                  45

Ile Tyr Gly Ala Ser Asn Arg Ala Thr Asp Ile Pro Asp Arg Phe Ser
 50                      55                  60

Gly Ser Gly Ser Gly Thr Asp Phe Thr Leu Thr Ile Arg Arg Leu Glu
 65                  70                  75                  80

Pro Glu Asp Ser Ala Val Tyr Tyr Cys Gln Gln Phe Ser Val Ser Pro
                 85                  90                  95

Trp Thr Phe Gly Gln Gly Thr Arg Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 40
<211> LENGTH: 456
<212> TYPE: PRT
<213> ORGANISM: Artificial Sequence
<220> FEATURE:
<223> OTHER INFORMATION: CT149_HC_Fab

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ser Phe Ser Thr Tyr
            20                  25                  30

Gly Val Ser Trp Val Arg Gln Ala Pro Gly Gln Gly Pro Glu Trp Val
        35                  40                  45

Gly Trp Ile Ser Ala Tyr Thr Gly Ile Thr Asp Tyr Ala Gln Lys Phe
 50                  55                  60

Gln Gly Arg Val Thr Leu Thr Thr Asp Ala Thr Thr Ala Thr Ala Phe
65                  70                  75                  80

Leu Asp Leu Arg Ser Leu Arg Pro Asp Asp Thr Ala Thr Tyr Phe Cys
                85                  90                  95

Ala Arg Asp Lys Val Gln Gly Arg Val Glu Val Gly Ser Gly Gly Arg
            100                 105                 110

His Asp Tyr Trp Gly Gln Gly Thr Leu Val Ile Val Ser Ser Ala Ser
        115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

```
His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
            195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Gly Leu His Asn His Tyr Thr Gln Lys
            435                 440                 445

Ser Leu Ser Leu Ser Pro Gly Lys
    450                 455

<210> SEQ ID NO 41
<211> LENGTH: 215
<212> TYPE: PRT
<213> ORGANISM: Artificial Sequence
<220> FEATURE:
<223> OTHER INFORMATION: CT164_LC_Fab

<400> SEQUENCE: 41

Glu Val Val Leu Thr Gln Ser Pro Gly Thr Leu Thr Leu Pro Pro Gly
1               5                   10                  15

Asp Arg Ala Thr Leu Ser Cys Arg Ala Ser His Ser Val Gly Ser Thr
            20                  25                  30

Tyr Ile Ala Trp Phe Gln Gln Lys Ser Gly Gln Ala Pro Arg Arg Leu
        35                  40                  45

Ile Tyr Gly Ala Ser Asn Arg Ala Thr Asp Ile Pro Asp Arg Phe Ser
    50                  55                  60

Gly Ser Gly Ser Gly Thr Asp Phe Thr Leu Thr Ile Arg Arg Leu Glu
65                  70                  75                  80
```

```
Pro Glu Asp Ser Ala Val Tyr Tyr Cys Gln Gln Phe Ser Val Ser Pro
                85                  90                  95

Trp Thr Phe Gly Gln Gly Thr Arg Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 42
<211> LENGTH: 456
<212> TYPE: PRT
<213> ORGANISM: Artificial Sequence
<220> FEATURE:
<223> OTHER INFORMATION: CT164_HC_Fab

<400> SEQUENCE: 42

Gln Val Gln Leu Val Gln Ser Gly Val Glu Val Lys Lys Pro Gly Ala
1               5                   10                  15

Ser Val Lys Val Ser Cys Lys Thr Ser Gly Tyr Pro Phe Ser Thr Tyr
                20                  25                  30

Gly Val Ser Trp Val Arg Gln Ala Pro Gly Gln Gly Leu Glu Trp Val
            35                  40                  45

Gly Trp Ile Ser Gly Tyr Thr Gly Ile Thr Asp Tyr Ala Gln Lys Ser
    50                  55                  60

Gln Gly Arg Val Thr Leu Thr Thr Asp Ala Ser Thr Ala Thr Ala Phe
65                  70                  75                  80

Leu Glu Leu Arg Ser Leu Arg Pro Asp Asp Thr Ala Thr Tyr Phe Cys
                85                  90                  95

Ala Arg Asp Lys Val Gln Gly Arg Val Glu Ala Gly Ser Gly Gly Arg
            100                 105                 110

His Asp Tyr Trp Gly Gln Gly Thr Leu Val Ile Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220
```

-continued

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
        260                 265                 270

Val Asp Val Ser His Glu Asp Pro Glu Val Lys Phe Asn Trp Tyr Val
    275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
        340                 345                 350

Arg Glu Pro Gln Val Tyr Thr Leu Pro Pro Ser Arg Asp Glu Leu Thr
    355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
        420                 425                 430

Ser Cys Ser Val Met His Glu Gly Leu His Asn His Tyr Thr Gln Lys
    435                 440                 445

Ser Leu Ser Leu Ser Pro Gly Lys
450                 455

<210> SEQ ID NO 43
<211> LENGTH: 215
<212> TYPE: PRT
<213> ORGANISM: Artificial Sequence
<220> FEATURE:
<223> OTHER INFORMATION: CT166_LC_Fab

<400> SEQUENCE: 43

Glu Val Val Leu Thr Gln Ser Pro Gly Thr Leu Ala Leu Pro Pro Gly
1               5                   10                  15

Glu Arg Ala Thr Leu Ser Cys Arg Ala Ser His Ser Ile Gly Ser Thr
            20                  25                  30

Tyr Ile Ala Trp Tyr Gln Gln Lys Ser Gly Gln Ala Pro Arg Arg Leu
        35                  40                  45

Ile Tyr Gly Ala Ser Asn Arg Ala Ser Asp Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Ser Ala Val Tyr Tyr Cys Gln Gln Phe Ser Val Ser Pro
            85                  90                  95

Trp Thr Phe Gly Gln Gly Thr Arg Val Glu Ile Lys Arg Thr Val Ala
        100                 105                 110

Ala Pro Ser Val Phe Ile Phe Pro Pro Ser Asp Glu Gln Leu Lys Ser
    115                 120                 125

```
Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 44
<211> LENGTH: 456
<212> TYPE: PRT
<213> ORGANISM: Artificial Sequence
<220> FEATURE:
<223> OTHER INFORMATION: CT166_HC_Fab

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ser Phe Ser Thr Tyr
            20                  25                  30

Gly Val Ser Trp Val Arg Gln Ala Pro Gly Gln Gly Leu Glu Trp Val
        35                  40                  45

Gly Trp Ile Ser Gly Tyr Thr Gly Ile Thr Asp Tyr Ala Gln Lys Phe
    50                  55                  60

Gln Gly Arg Val Thr Leu Thr Thr Asp Ala Thr Thr Ala Thr Ala Phe
65                  70                  75                  80

Leu Glu Leu Arg Ser Leu Arg Pro Asp Thr Ala Thr Tyr Phe Cys
                85                  90                  95

Ala Arg Asp Lys Val Gln Gly Arg Val Glu Val Gly Ser Gly Gly Arg
                100                 105                 110

His Asp Tyr Trp Gly Gln Gly Thr Leu Val Ile Val Ser Ser Ala Ser
            115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270
```

```
Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
                385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Gly Leu His Asn His Tyr Thr Gln Lys
        435                 440                 445

Ser Leu Ser Leu Ser Pro Gly Lys
    450                 455

<210> SEQ ID NO 45
<211> LENGTH: 648
<212> TYPE: DNA
<213> ORGANISM: Artificial Sequence
<220> FEATURE:
<223> OTHER INFORMATION: CT147_LC_Fab

<400> SEQUENCE: 45
gagattgtgt tgactcagtc tccaggcacc ctgtctgtgt ctccagggga agagccacc      60 ctctcctgca gggccagtcg gcgcgttggc agcacctact tagcctggta ccagcagaaa     120
cctggccagg ctcccaggcg cctcatctat ggtgcatcca gcagggccgc tggcatccca     180
gacaggttca gtggcactgg gtctgggaca gacttcactc tcaccatcag cagggtggac     240
cctgaagatt ttgcggtata ttactgtcag cagtatgctg cctcaccgtg acgttcggc      300 caagggacca cggtggagat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag      600
ggcctgagct cgcccgtcac aaagagcttc aacaggggag agtgttag                  648

<210> SEQ ID NO 46
<211> LENGTH: 1371
<212> TYPE: DNA
<213> ORGANISM: Artificial Sequence
<220> FEATURE:
<223> OTHER INFORMATION: CT147_HC_Fab

<400> SEQUENCE: 46
caggttcagc tggtgcagtc tggaggtgag ctgaagaagc ctggggcctc agtgagggtc      60
```

```
tcctgtaagg cttctggcta ccctttacc acctatggca tcagctgggt gcgacaggcc      120
cctggacaag gccttgagtg ggtgggatgg atcagcgctt atactggaaa tacagactat    180
gcacagaagg tccagggcag agtaaccatg accacggaca catccacgag cacagcctac    240
atggagctga ggagcctcac atctgacgac acggccgtct attactgtgc gagagataag    300
gtccaggggc gcgttgaagc gggaagtggg ggccggcatg actactgggg ccagggaacc    360
ctggtcaccg tctcctcagc ctccaccaag ggcccatcgg tcttccccct ggcaccctcc    420
tccaagagca cctctggggg cacagcggcc ctgggctgcc tggtcaagga ctacttcccc    480
gaaccggtga cggtgtcgtg gaactcaggc gccctgacca gcggcgtgca caccttcccg    540
gctgtcctac agtcctcagg actctactct ctcagcagcg tggtgaccgt gccctccagc    600
agcttgggca cccagaccta catctgcaac gtgaatcaca agcccagcaa caccaargtg    660
gacaagaaag ttgagcccaa atcttgtgac aaaactcaca catgcccacc gtgcccagca    720
cctgaactcc tggggggacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta cgtggacggc gtggaggtgc ataatgccaa gacaaagccg    900
cgggaggagc agtacaacag cacgtaccgt gtggtcagcg tcctcaccgt cctgcaccag    960
gactggctga atggcaagga gtacaagtgc aaggtctcca acaaagccct cccagccccc   1020
atcgagaaaa ccatctccaa agccaaaggg cagccccgag aaccacaggt gtacaccctg   1080
cccccatccc gggatgagct gaccaagaac caggtcagcc tgacctgcct ggtcaaaggc   1140
ttctatccca gcgacatcgc cgtggagtgg gagagcaatg ggcagccgga gaacaactac   1200
aagaccacgc ctcccgtgct ggactccgac ggctccttct tcctctacag caagctcacc   1260
gtggacaaga gcaggtggca gcaggggaac gtcttctcat gctccgtgat gcatgagggt   1320
ctgcacaacc actacacgca gaagagcctc tccctgtctc cgggtaaatg a            1371
```

<210> SEQ ID NO 47
<211> LENGTH: 648
<212> TYPE: DNA
<213> ORGANISM: Artificial Sequence
<220> FEATURE:
<223> OTHER INFORMATION: CT149_LC_Fab

<400> SEQUENCE: 47

```
gaagttgtgt tgacacagtc tcccggcacc ctggctttgc ctccagggga aagagccacc     60
ctctcctgca gggccagtca ccgtgttggc agcacctaca tagcctggta tcagcagaag    120
tctggccagg ctcccaggcg cctcatctat ggtgcatcca cagggccac tgacatccca    180 gacaggttca gtggcagtgg gtccgggaca gacttcactc tcaccatcag agactggag    240 cctgaagatt ctgcagtgta ttactgtcag cagtttagtg tttccgtg acgttcggc      300 caagggacca gggtggaaat caagcgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagacta cgagaaacac aaagtctacg cctgcgaagt cacccatcag    600
ggcctgagct cgcccgtcac aaagagcttc aacaggggag agtgttag                648
```

<210> SEQ ID NO 48

```
<211> LENGTH: 1371
<212> TYPE: DNA
<213> ORGANISM: Artificial Sequence
<220> FEATURE:
<223> OTHER INFORMATION: CT149_HC_Fab

<400> SEQUENCE: 48
caggttcagc tggtgcagtc tggagctgag gtgaagaagc ctggggcctc agtgaaggtc      60
tcctgcaaga cttctggtta ttccttttcc acttatggag tcagttgggt ccgacaggcc     120
cccggacaag ggcctgagtg ggtgggatgg atcagcgctt acactggtat cacagactac     180
gcacagaagt tcagggcag  agtcactctg accacagacg caaccacggc caccgccttc     240
ctggacctga ggagtctgag acctgacgac acggccacgt atttctgtgc gagagataag     300
gtgcaggggc gcgttgaagt gggatctggg ggtcgtcatg actactgggg cagggaacc      360
ctggtcatcg tctcctcagc ctccaccaag ggcccatcgg tcttcccct  ggcaccctcc     420
tccaagagca cctctggggg cacagcggcc ctgggctgcc tggtcaagga ctacttcccc     480
gaaccggtga cggtgtcgtg gaactcaggc gccctgacca gcggcgtgca ccttcccg      540
gctgtcctac agtcctcagg actctactcc ctcagcagcg tggtgaccgt gccctccagc     600
agcttgggca cccagaccta catctgcaac gtgaatcaca agcccagcaa caccaaggtg     660
gacaagaaag ttgagcccaa atcttgtgac aaaactcaca catgcccacc gtgcccagca     720
cctgaactcc tggggggacc gtcagtcttc ctcttccccc caaaacccaa ggacaccctc     780
atgatctccc ggacccctga ggtcacatgc gtggtggtgg acgtgagcca cgaagaccct     840
gaggtcaagt tcaactggta cgtggacggc gtggaggtgc ataatgccaa gacaaagccg     900
cgggaggagc agtacaacag cacgtaccgt gtggtcagcg tcctcaccgt cctgcaccag     960
gactggctga atggcaagga gtacaagtgc aaggtctcca acaaagccct cccagccccc    1020
atcgagaaaa ccatctccaa agccaaaggg cagccccgag aaccacaggt gtacaccctg    1080
cccccatccc gggatgagct gaccaagaac caggtcagcc tgacctgcct ggtcaaaggc    1140
ttctatccca gcgacatcgc cgtggagtgg gagagcaatg ggcagccgga gaacaactac    1200
aagaccacgc ctcccgtgct ggactccgac ggctccttct tcctctacag caagctcacc    1260
gtggacaaga gcaggtggca gcaggggaac gtcttctcat gctccgtgat gcatgagggt    1320
ctgcacaacc actacacgca gaagagcctc tccctgtctc cgggtaaatg a             1371

<210> SEQ ID NO 49
<211> LENGTH: 648
<212> TYPE: DNA
<213> ORGANISM: Artificial Sequence
<220> FEATURE:
<223> OTHER INFORMATION: CT164_LC_Fab

<400> SEQUENCE: 49
gaagttgtgt tgacgcagtc tcccggcacc ctgactttgc ctccagggga cagagccacc      60
ctctcctgca gggccagtca cagtgttggc agcacctaca tagcctggtt tcagcagaag     120
tctggccagg ctcccaggcg cctcatctat ggtgcatcca cagggccact gacatccca      180
gacaggttca gtggcagtgg gtccgggaca gacttcactc tcaccatcag agactggag      240
cctgaagatt ctgcagtgta ctactgtcag cagtttagtg tttcaccgtg gacgttcggc     300
caagggacca gggtggaaat caagcgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
```

```
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacaggggag agtgttag                   648
```

<210> SEQ ID NO 50
<211> LENGTH: 1371
<212> TYPE: DNA
<213> ORGANISM: Artificial Sequence
<220> FEATURE:
<223> OTHER INFORMATION: CT164_HC_Fab

<400> SEQUENCE: 50

```
caggttcagc tggtccagtc tggagtagag gtgaagaagc ctggggcctc agtgaaggtc       60
tcctgcaaga cttctggtta ccgtttttcc acttatggag tcagctgggt ccgacaggcc      120
cctggacaag gcttgagtg gtgggatgg atcagcggtt atactggtat cacagactac        180
gcacagaagt ctcagggcag agtcactctg acgacagacg caagcacggc caccgccttc      240
ttggagctga ggagtctgag gcctgacgac acggccacct attttgtgc gagagacaaa       300 gtgcaggggc gcgttgaagc gggatctggg ggtcgtcacg actactgggg acagggaacc      360
ctggtcatcg tctcctcagc ctccaccaag ggcccatcgg tcttccccct ggcaccctcc      420
tccaagagca cctctggggg cacagcggcc ctgggctgcc tggtcaagga ctacttcccc      480
gaaccggtga cggtgtcgtg gaactcaggc gccctgacca gcggcgtgca ccttcccg        540 gctgtcctac agtcctcagg actctactcc ctcagcagcg tggtgaccgt gccctccagc      600
agcttgggca cccagaccta catctgcaac gtgaatcaca agcccagcaa caccaaggtg      660
gacaagaaag ttgagcccaa atcttgtgac aaaactcaca catgcccacc gtgcccagca      720
cctgaactcc tggggggacc gtcagtcttc ctcttccccc caaaacccaa ggacaccctc      780
atgatctccc ggacccctga ggtcacatgc gtggtggtgg acgtgagcca cgaagaccct      840
gaggtcaagt tcaactggta cgtggacggc gtggaggtgc ataatgccaa gacaaagccg      900
cgggaggagc agtacaacag cacgtaccgt gtggtcagcg tcctcaccgt cctgcaccag      960
gactggctga atggcaagga gtacaagtgc aaggtctcca acaaagccct cccagccccc     1020
atcgagaaaa ccatctccaa agccaaaggg cagccccgag aaccacaggt gtacaccctg     1080
cccccatccc gggatgagct gaccaagaac caggtcagcc tgacctgcct ggtcaaaggc     1140
ttctatccca gcgacatcgc cgtggagtgg gagagcaatg ggcagccgga gaacaactac     1200
aagaccacgc ctcccgtgct ggactccgac ggctccttct tcctctacag caagctcacc     1260
gtggacaaga gcaggtggca gcaggggaac gtcttctcat gctccgtgat gcatgagggt     1320
ctgcacaacc actacacgca gaagagcctc tccctgtctc cgggtaaatg a             1371
```

<210> SEQ ID NO 51
<211> LENGTH: 648
<212> TYPE: DNA
<213> ORGANISM: Artificial Sequence
<220> FEATURE:
<223> OTHER INFORMATION: CT166_LC_Fab

<400> SEQUENCE: 51

```
gaagttgtgt tgacgcagtc tcccggcacc ctggctttgc ctccagggga aagagccacc       60
ctctcctgca gggccagtca cagtattggc agcacctaca tagcctggta tcagcagaag      120
tctggccagg ctcccaggcg cctcatctat ggtgcatcca cagggcctc tgacatccca       180
```

-continued

```
gacaggttca gtggcagtgg gtccgggaca gacttcactc tcaccatcag gagactggag    240
cctgaagatt ctgcagtgta ttactgtcag cagtttagtg tttccccgtg gacgttcggc    300
caagggacca gggtggaaat caagcgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgttag                 648

<210> SEQ ID NO 52
<211> LENGTH: 1371
<212> TYPE: DNA
<213> ORGANISM: Artificial Sequence
<220> FEATURE:
<223> OTHER INFORMATION: CT166_HC_Fab

<400> SEQUENCE: 52
caggttcagc tggtgcagtc tggagctgag gtgaagaagc ctggggcctc agtgaaggtc     60
tcctgcaaga cttctggtta ttccttttcc acttatggag tcagctgggt ccgacaggcc    120
cctggacaag gcttgagtg ggtgggatgg atcagcggtt acactggtat cacagactac    180
gcacagaagt ttcagggcag agtcactctg accacagacg caaccacggc caccgccttc    240
ctggagctga ggagtctgag acctgacgac acggccacct atttctgtgc gagagataag    300
gtgcaggggc gcgttgaagt gggatctggg ggtcgtcatg actactgggg acagggaacc    360
ctggtcatcg tctcctcagc ctccaccaag ggcccatcgg tcttccccct ggcaccctcc    420
tccaagagca cctctggggg cacagcggcc ctgggctgcc tggtcaagga ctacttcccc    480
gaaccggtga cggtgtcgtg gaactcaggg gccctgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagaaag ttgagcccaa atcttgtgac aaaactcaca catgcccacc gtgcccagca    720
cctgaactcc tggggggacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta cgtggacggc gtggaggtgc ataatgccaa gacaaagccg    900
cgggaggagc agtacaacag cacgtaccgt gtggtcagcg tcctcaccgt cctgcaccag    960
gactggctga atggcaagga gtacaagtgc aaggtctcca acaaagccct cccagccccc   1020
atcgagaaaa ccatctccaa agccaaaggg cagccccgag aaccacaggt gtacaccctg   1080
cccccatccc gggatgagct gaccaagaac caggtcagcc tgacctgcct ggtcaaaggc   1140
ttctatccca gcgacatcgc cgtggagtgg gagagcaatg gcagccgga gaacaactac   1200 aagaccacgc ctcccgtgct ggactccgac ggctccttct tcctctacag caagctcacc   1260
gtggacaaga gcaggtggca gcaggggaac gtcttctcat gctccgtgat gcatgagggt   1320
ctgcacaacc actacacgca gaagagcctc tccctgtctc cgggtaaatg a            1371
```